(12) United States Patent
Jia et al.

(10) Patent No.: US 10,612,843 B2
(45) Date of Patent: Apr. 7, 2020

(54) CIRCULATING FLUIDIZED BED APPARATUS

(71) Applicant: KUNMING TEKANG TECHNOLOGY CO., LTD., Yunnan (CN)

(72) Inventors: Ping Jia, Yunnan (CN); Yunjie Yang, Yunnan (CN); Wanheng Hu, Yunnan (CN); Yunjing Jia, Yunnan (CN)

( * ) Notice: Subject to any disclaimer, the term of this patent is extended or adjusted under 35 U.S.C. 154(b) by 954 days.

(21) Appl. No.: 15/108,585

(22) PCT Filed: Dec. 30, 2014

(86) PCT No.: PCT/CN2014/095514
§ 371 (c)(1),
(2) Date: Jun. 28, 2016

(87) PCT Pub. No.: WO2015/101279
PCT Pub. Date: Jul. 9, 2015

(65) Prior Publication Data
US 2016/0327338 A1    Nov. 10, 2016

(30) Foreign Application Priority Data
Dec. 31, 2013    (CN) .......................... 2013 1 0748462

(51) Int. Cl.
*B07B 11/02* (2006.01)
*F26B 3/08* (2006.01)
(Continued)

(52) U.S. Cl.
CPC ................ *F26B 3/08* (2013.01); *A61L 2/10* (2013.01); *B07B 11/02* (2013.01); *F26B 21/02* (2013.01)

(58) Field of Classification Search
CPC .. B07B 9/00; B07B 9/02; B07B 11/02; B07B 11/06; F26B 3/08; F26B 21/02;
(Continued)

(56) References Cited

U.S. PATENT DOCUMENTS

| 790,162 A | * | 5/1905 | Trump | ...................... F26B 3/08 |
|           |   |        |       | 34/591 |
| 3,524,544 A | * | 8/1970 | Jäger | ...................... B02C 23/22 |
|             |   |        |       | 209/11 |

(Continued)

*Primary Examiner* — Joseph C Rodriguez
(74) *Attorney, Agent, or Firm* — Prakash Nama; Global IP Services, PLLC

(57) ABSTRACT

A circulating fluidized bed apparatus, using fans, circulating pipes, functional branches and feeding pipes sequentially connected to form one or more circulating channels; the fans and jet streams generated thereby disperse materials into a fluidized state; the fluidized materials circulate and flow at a high speed in the circulating channels to achieve the objectives of the process, efficiently realizing operations such as drying, smashing, evaporating and distilling, concentrating, sieving, mixing, and ultraviolet sterilizing of powdered materials, realizing quick drying at normal temperature, and quickly preparing fresh plant materials into powdered materials at normal temperature. All the operations are performed by one apparatus, thus reducing equipment investment, simplifying production process steps, improving product quality, reducing production costs, and having low energy consumption, wide application and a simple structure.

14 Claims, 10 Drawing Sheets

(51) Int. Cl.
*F26B 21/02* (2006.01)
*A61L 2/10* (2006.01)

(58) Field of Classification Search
CPC .... F26B 21/024; F26B 21/028; F26B 21/083; B02C 23/10; A61L 2/10
See application file for complete search history.

(56) References Cited

U.S. PATENT DOCUMENTS

| | | | | |
|---|---|---|---|---|
| 3,892,682 | A | * | 7/1975 | Punwani ............... C01B 13/083 252/372 |
| 3,972,808 | A | * | 8/1976 | Manley ..................... B07B 4/02 209/133 |
| 4,037,330 | A | * | 7/1977 | Kemmetmuller ....... C10B 39/02 34/428 |
| 4,678,560 | A | * | 7/1987 | Stole ........................ B07B 9/00 209/138 |
| 4,721,457 | A | * | 1/1988 | Areaux ................... C22B 1/005 34/591 |
| 6,203,595 | B1 | * | 3/2001 | Edlinger ................ B02C 19/06 423/430 |
| 6,298,579 | B1 | * | 10/2001 | Ichitani .................... B03B 4/00 209/154 |
| 6,415,528 | B2 | * | 7/2002 | Holler .................... F26B 9/063 165/104.16 |
| 6,910,283 | B1 | * | 6/2005 | Reddy .................... D21F 5/182 162/207 |
| 8,627,960 | B2 | * | 1/2014 | Valerio .................... B07B 7/01 209/139.1 |
| 9,132,432 | B2 | * | 9/2015 | Andersen ............... B03B 9/061 |

\* cited by examiner

CIRCULATING FLUIDIZED BED APPARATUS

BACKGROUND OF THE INVENTION

The present invention relates to a circulating fluidized bed apparatus, and belongs to the technical fields such as circulating fluidized beds, chemical engineering and food and pharmaceutical processing.

Since high-humidity high-viscosity materials are difficult to disperse, the materials will be attached to a machine part to be the difficulty in the drying industry. A high-viscosity quick drying machine in the Chinese patent CN2011104233878 of Shijiazhuang NSTL Engineering Technology Co., Ltd. mainly comprises a driving motor, a mainframe, flying teeth, crushing teeth and a turbofan and the like; the high-viscosity quick drying machine is a cylinder, the outer wall is provided with a heating outer sleeve and is subject to heat preservation through a heat insulation material, a flying tooth device makes the high-humidity high-viscosity material continuously dispersed into particles so as to increase heat transfer area, thus it is guaranteed that the materials are not attached to device components, and the high-humidity high-viscosity materials are dried. Mineral grinding is an important production process in cement production; the powder grinding operation in cement production generally refers to grinding the material by a mill and then separating fine powder through a powder selecting machine. Similar power grinding operations are widely used for industries such as metallurgy, chemical engineering and building materials. Due to the fact that fine powder cannot be separated timely through an existing mineral grinding process, the efficiency of the mill is lowered to some extent, and energy consumption is increased; the powder grinding and powder selection operations are finished in different devices, the process flow is long, and the equipment cost is high.

At present, a method for drying and powder grinding of medicine and food materials generally comprises the steps of first drying the materials and then grinding the materials, and the method has the problems of high operation temperature, long operation duration, high loss of effective ingredients, pollution in the production process, etc.; and methods and devices of performing evaporation and distillation, concentration, mixing, screening and sterilization operations and the like have the shortcomings that the energy consumption is high, the adaptability is not wide enough, and the product quality is not good enough.

A molecular sieve dryer is a device which utilizes molecular sieves as adsorbents to dehydrate gas. Molecular sieves of different types have selectivity in absorbing different gases, and by utilizing the characteristics, the molecular sieve dryer is also used for separating specific ingredients out of gas. FIG. 7 illustrates an embodiment of the molecular sieve dryer and the molecular sieve dryer comprises a first molecular sieve container 95, a second molecular sieve container 96, an inlet air pipe 97, a regeneration branch 98 and an outlet air pipe 99. A port of a tee on the inlet air pipe 97 is an air inlet 107 of the molecular sieve dryer, and a port of a tee on the outlet air pipe 99 is an air outlet 120 of the molecular sieve dryer. Molecular sieves and heating devices are installed in the molecular sieve containers. When the first molecular sieve container 95 is in a working state, the molecular sieve in the first molecular sieve container 95 adsorbs moisture and/or specific ingredients in gas so as to dry the gas and/or separate the specific ingredients; meanwhile, the heating device in the second molecular sieve container is started; a vacuum pump on the regeneration branch 98 vacuumizes the second molecular sieve container 96, so that the molecular sieve in the second molecular sieve container 96 is regenerated, and the adsorbed moisture and/or the specific ingredients are adsorbed; when the molecular sieve in the first molecular sieve container 95 is saturated, the second molecular sieve container works instead, and the molecular sieve in the first molecular sieve container is regenerated. A gas treatment apparatus made of molecular sieves has already been widely applied to drying of medium and high pressure gas, separation of specific ingredients and enrichment operation of the specific ingredients. However, the gas treatment apparatus is seldom applied to low pressure gas such as 5000-2000 Pa low pressure gas generated by a fan and seldom used for providing a low moisture and low oxygen content operating medium in drying operations.

An ejector is a device which utilizes a nozzle to spray high-pressure fluid into a mixing pipe, so as to form negative pressure around the nozzle and suck materials through the negative pressure to mix the high-pressure fluid and the sucked materials. When the high-pressure fluid is gas, the ejector can also be used for dispersing liquid and powdered materials into a fluidized state and conveying the materials. FIG. 15 illustrates an embodiment of the ejector, and among markers in the figure, there is a nozzle 270, a vacuum chamber 271, a mixing pipe 272, a diffusing pipe 273, a mixture outlet 274, a nozzle outlet 275, a suction inlet 276 and a high-pressure fluid inlet 277.

A fan is a gas conveying device. Materials are certainly smashed under the an impact effect of fan impellers while the fluidized materials pass through the fan to be conveyed, and under the conditions that the structural strength of the fan meets the requirements, an unexpected remarkable effect can be achieved by using the fan to convey and smash the fluidized materials. However, due to the regulations of most of fan manuals on limitation of dust content in gas conveyed by fans, it leads to the prejudice that the fan cannot be used for directly conveying the fluidized materials, and there are few methods of conveying the fluidized materials through the inside of the fan and methods of smashing through fans.

Apparatuses for powdered material drying, screening and sterilization are disclosed in Chinese patents ZL2010101628876, ZL2011001629417 and ZL2010101628984 respectively. The three inventions are improved based on a fluidized drying machine, are complex in structure and cannot work reliably due to poor circulation. However, the concept of a circulating fluidized bed elaborated in the present inventions is of great significance. The conventional circulating fluidized bed mostly refers to a combustion technology applied to a coal burning boiler, and the three Chinese patents expands the concept of the circulating fluidized bed. The circulating fluidized bed is improved in the Chinese patent 2013107484627, the circulation problem of low-viscosity powdered materials is solved, and the characteristics that the circulating fluidized bed is low in energy consumption, can perform large-scale normal temperature drying quickly and is high in efficiency are highlighted. However, due to the problems that viscous materials are attached to a material-gas separator bag, large mineral materials damage the fan and no economically feasible method is available to provide inlet air stream conforming to the process requirements, the circulating fluidized bed cannot be used for processing high-humidity high-viscosity materials and grinding large mineral materials, the problems occurring in drying, smashing, evaporation and distillation operations and the like cannot be solved, and the requirements of reducing production costs in all industries and improving product quality cannot be met.

BRIEF SUMMARY OF THE INVENTION

An objective of the present invention is to provide a circulating fluidized bed apparatus which is simple in structure, works reliably and efficiently achieve process operations such as drying, screening, smashing, mixing, evaporation and distillation, so as to solve part of problems as described in the technical background.

The technical solution adopted by the present invention is as follows: a circulating fluidized bed apparatus comprising a fan, a circulating pipe, a functional branch and a feeding pipe, wherein the fan is a power device and is used for dispersing materials into a fluidized state and making the materials circulate and flow at a high speed in a circulating channel; the head end of the circulating pipe is an inlet of the circulating pipe, and the circulating pipe is provided with a functional branch port; the functional branch is used for achieving specific process objectives; the head end of the functional branch is an inlet, and the tail end of the functional branch is an outlet; the feeding pipe is used for feeding to the circulating pipe the materials discharged out of the functional branch port; the head end of the feeding pipe is an inlet of the feeding pipe and is also an air inlet of the circulating fluidized bed apparatus, and the tail end of the feeding pipe is an outlet of the feeding pipe; the feeding pipe is provided with a functional branch port and a feeding port, and the feeding port is provided with a feeding device; the aforementioned components are communicated in such a sequence as the air outlet of the fan, the inlet of the circulating pipe, the functional branch port of the circulating pipe, the inlet of the functional branch, the outlet of the functional branch, the functional branch port of the feeding pipe, the outlet of the feeding pipe and the air inlet of the fan to form the circulating channel.

As a further restriction of the present invention, the functional branch is one or more selected from a group comprising a cyclone dust collector branch, a bag type dust collector branch, a screen drum branch and a molecular sieve dryer branch. The cyclone dust collector branch at least comprises a cyclone dust collector and is formed by partially or all connecting an inlet valve, the cyclone dust collector and an ash discharging valve installed on an ash discharging port of the cyclone dust collector in sequence; an air inlet of the cyclone dust collector is an inlet of the cyclone dust collector, an ash discharging port of the cyclone dust collector is an outlet of the cyclone dust collector, an air outlet of the cyclone dust collector is both the air outlet of the cyclone dust collector and an air outlet of the cyclone dust collector branch, and the cyclone dust collector branch is used for impurity separation and material classification or used as a material-gas separation device. The bag type dust collector branch at least comprises a bag type dust collector and is formed by partially or all connecting an inlet valve, a conveying tee, the bag type dust collector, a discharging tee and a regulating valve in sequence; a third port of the conveying tee is provided with a conveying valve, and a third port of the discharging tee is provided with a discharging valve; the bag type dust collector has the same structure as the bag type dust collector as described in the Chinese patent 2013107484627; an air inlet of the bag type dust collector is an inlet of the bag type dust collector, an ash discharging port of the bag type dust collector is an outlet of the bag type dust collector, an air outlet of the bag type dust collector is both the air outlet of the bag type dust collector and an air outlet of the bag type dust collector branch, and the bag type dust collector branch is used for material-gas separation. The screen drum branch at least comprises a screen drum and is formed by partially or all connecting an inlet valve, the screen drum, a slag-discharging tee and a regulating valve in sequence; a third port of the slag-discharging tee is provided with a slag-discharging valve, and the screen drum has the same structure as the screen drum in the Chinese patent 2013107484627; an air inlet of the screen drum is an inlet of the screen drum, an ash discharging port of the screen drum is an outlet of the screen drum; an air outlet of the screen drum is both the air outlet of the screen drum and a screen underflow discharging port and is also an air outlet of the screen drum branch, and the screen drum branch is used for meshed air stream screening; the molecular sieve dryer branch at least comprises a molecular sieve dryer and is formed by partially or all connecting an inlet valve, the molecular sieve dryer and a regulating valve in sequence; and the molecular sieve dryer branch is used for separating moisture, oxygen or specific ingredients in the operating medium.

Preferably, when the cyclone dust collector branch is used for impurity separation and material classification, the ratio of the diameter of a barrel of the cyclone dust collector to the height of a cone is larger than 1, and a separating drum for separating lower vortex air stream and upper vortex air stream is arranged in the barrel. The upper end of the separating drum is connected with an upper end cover of the cyclone dust collector, the lower end of the separating drum extends into the cone, and the particle size of fine powder separated from the cyclone dust collector can be adjusted by adjusting the diameter of the separating drum and the distance between the lower end face of the separating drum and the cone. When the cyclone dust collector branch serves as a primary material-gas separation device, the ratio of the sectional area of the air inlet of the cyclone dust collector to the sectional area of the ash discharging port is larger than 2.

In order to achieve operations on various materials, the feeding device is a feeding valve or/and an atomizer or a feeder or an extruding machine; the atomizer is used for feeding liquid materials; and the feeder is preferably a screw feeder and is used for feeding to-be-processed materials and/or materials separated from the functional branch into the feeding pipe at a constant speed. When the screw feeder is used for feeding the to-be-processed materials and/or the materials separated from the functional branch into the feeding pipe at a constant speed, a conveying pipe of the screw feeder is provided with a functional branch port, a feeding port and a discharging port; the functional branch port is connected with the functional branch outlet, and the discharging port is connected with the functional branch port on the feeding pipe; and the extruding machine is used for causing materials which are difficult to disperse and cannot be pumped to be extruded into a line shape and feeding the materials into the feeding pipe.

The present invention may further be implemented as follows: the feeding pipe is a conveyor which is a screw conveyor, and a conveying pipe of the screw conveyor is provided with a functional branch port and a discharging port; all the components are communicated in such a sequence as the functional branch port of the circulating pipe, the functional branch inlet, the functional branch outlet, the functional branch port of the screw conveyor and the discharging port of the screw conveyor inserted into the inlet of the circulating pipe so as to form the circulating channel, the air inlet of the fan is connected with the air outlet of the functional branch through a pipe, the gap between the discharging port of the screw conveyor and the inlet of the circulating pipe is an air inlet of the circulating fluidized bed apparatus, and the feeding port is arranged on the conveying pipe of the screw conveyor or the circulating pipe; or, a feeding port is at the position of the circulating pipe close to the inlet, the feeding pipe is a screw conveyor, a conveying pipe of the screw conveyor is provided with a functional branch port and a discharging port; all the components are communicated in such a sequence as the functional branch port of the circulating pipe, the inlet of the functional branch, the outlet of the functional branch, the functional branch port of the screw conveyor, the discharging port of the screw conveyor and the feeding port of the circulating pipe to form the circulating channel; the air outlet of the fan is connected with the inlet of the circulating pipe, the air inlet of the fan is an air inlet of the circulating fluidized bed apparatus, and a feeding port is arranged on the conveying pipe of the screw conveyor.

The present invention may also be implemented as follows: the feeding pipe is an ejector which is provided with a suction inlet, a mixture outlet and a high-pressure fluid inlet; the suction inlet is a functional branch port of the feeding pipe; all the components are communicated in such a sequence as the functional branch port of the circulating pipe, the inlet of the functional branch, the outlet of the functional branch, the suction inlet and the mixture outlet inserted into the inlet of the circulating pipe so as to form the circulating channel, the air inlet of the fan is connected with the air outlet of the functional branch through a pipe, the high-pressure fluid inlet is communicated with a high pressure air source, the gap between the mixture outlet and the inlet of the circulating pipe is an air inlet of the circulating fluidized bed apparatus, and the feeding port is arranged on the suction inlet or the circulating pipe; or, a feeding port is arranged at the position of the circulating pipe close to the inlet, and the feeding pipe is an ejector which is provided with a suction inlet, a mixture outlet and a high-pressure fluid inlet; the suction inlet is a functional branch port of the feeding pipe, and all the components are communicated in such a sequence as the functional branch port of the circulating pipe, the inlet of the functional branch, the outlet of the functional branch, the suction inlet, the mixture outlet and the feeding port of the circulating pipe to form a circulating channel; the air outlet of the fan is connected with the inlet of the circulating pipe, the high-pressure fluid inlet is communicated with the high pressure air source, the air inlet of the fan is an air inlet of the circulating fluidized bed apparatus, and the feeding port is arranged on the suction inlet.

For convenience in material discharging, the circulating pipe is further provided with a discharging port, and the discharging port is provided with a discharging valve; and/or, the cyclone dust collector is provided with a discharging port, and the discharging port is provided with a discharging valve; and/or, in the circulating fluidized bed apparatus with a bag type dust collector branch, the bag type dust collector branch is disconnected with the feeding pipe and a planet discharging valve is added at the tail end of the bag type dust collector branch, and materials collected by the bag type dust collector branch are discharged out of the planet discharging valve; or, an inlet of a discharging tee of the bag type dust collector branch is connected with an ash discharging port of the bag type dust collector, a second port of the discharging tee is provided with a planet discharging valve, a regulating valve is arranged on a third port of the discharging tee; a bend is arranged in the discharging tee, one end of the bend is connected with the third port inside the discharging tee, and the other end of the bend is arranged in the second port in a suspended mode, and materials collected by the bag type dust collector branch are discharged through the planet discharging valve; and/or, in the circulating fluidized bed apparatus with the screen drum branch, an inlet of a slag-discharging tee of the screen drum branch is connected with the ash-discharging port of the screen drum, the second port of the slag-discharging tee is provided with a planet discharging valve, a regulating valve is arranged on the third port of the slag-discharging tee, a bend is arranged in the slag-discharging tee, one end of the bend is connected with the third port inside the slag-discharging tee, the other end of the bend is arranged in the second port in a suspended mode, and materials collected by the screen drum branch are discharged through the planet discharging valve.

In order to achieve efficient grinding of mineral materials, a mill and a feeding pipe rear section are arranged between the outlet of the feeding pipe and the fan; the feeding pipe rear section is vertically arranged and is a variable diameter pipe, and the pipe diameter of the inlet end is larger than that of the outlet end; the outlet of the feeding pipe is connected with a feeding port of the mill, a discharging port of the mill is connected with an inlet of the feeding pipe rear section, an outlet of the feeding pipe rear section is connected with the air inlet of the fan, and the feeding port on the feeding pipe is next to the outlet of the feeding pipe.

In order to achieve air stream drying of high-humidity high-viscosity materials such as a fresh plant materials, as an improvement of the present invention, a circulating pipe front section and a second fan are arranged between the air outlet of the fan and the inlet of the circulating pipe, an inlet of the circulating pipe front section is connected with the air outlet of the fan, an outlet of the circulating pipe front section is connected with an air inlet of the second fan, and an air outlet of the second fan is connected with the inlet of the circulating pipe; and/or, a feeding pipe rear section and a third fan are arranged between the outlet of the feeding pipe and the air inlet of the fan, the outlet of the feeding pipe is connected with the air inlet of the third fan, the air outlet of the third fan is connected with the inlet of the feeding pipe rear section, and the outlet of the feeding pipe rear section is connected with the air inlet of the fan.

In order to control the temperature in the apparatus, according to the present invention, the apparatus further comprises a regulating device. The regulating device comprises an inlet air stream temperature regulating device and/or a fan rotating speed regulating device. The inlet air stream temperature regulating device controls the temperature of inlet air stream through output signals of a temperature sensor installed on the circulating pipe, so that the temperature inside the apparatus does not exceed a set temperature; and the fan rotating speed regulating device is used for regulating the rotating speed of the fan so as to control heat produced by converting kinetic energy of the fan, so that the temperature inside the apparatus does not exceed a set temperature.

In order to achieve ultraviolet sterilization of powdered materials, as an improvement of the present invention, an ultraviolet sterilization lamp tube for achieving ultraviolet sterilization of the powdered materials is installed in the circulating channel.

In order to reduce moisture of inlet air stream, accelerate drying speed and/or reduce oxygen content in the inlet air stream to achieve protective operations, the circulating fluidized bed apparatus is further provided with a molecular sieve dryer to serve as an inlet gas treatment device; an air outlet of the molecular sieve dryer is connected with the air inlet of the circulating fluidized bed apparatus and a blowback air source supercharging device through a supply air duct; natural air is adopted by the molecular sieve dryer to serve as inlet air, an air inlet of an inlet air pipe is communicated with the outside of the apparatus; or, exhaust discharged out of the bag type dust collector branch is adopted by the molecular sieve dryer to serve as inlet air, the air inlet is connected with the air outlet of the bag type dust collector branch through an inlet air pipe, the air inlet or the air outlet is provided with a gas supply port, and the gas supply port is communicated with natural air outside the apparatus or communicated with a special gas source.

In order to collect screen underflow of the screen drum branch through the bag type dust collector branch, in the apparatus with the bag type dust collector branch and the screen drum branch, a conveying pipe for feeding to the bag type dust collector branch the materials discharged out of the screen drum branch is arranged, the inlet of the conveying pipe is connected with the air outlet of the screen drum branch, and the outlet of the conveying pipe is connected with the inlet of a conveying valve of the bag type dust collector branch.

In order to perform evaporation and distillation and collect specific ingredients in the exhaust by the apparatus according to the present invention, the air outlet of the bag type dust collector branch is further provided with an exhaust treatment device, an inlet of the exhaust treatment device is connected with the air outlet of the bag type dust collector branch through a pipe, and the exhaust treatment device is a condenser or a device for collecting specific ingredients. Furthermore, in the apparatus with the exhaust treatment device and the inlet gas treatment device, the air inlet of the molecular sieve dryer is connected with the air outlet of the exhaust treatment device through a pipe.

Preferably, in the apparatus with the cyclone dust collector branch, the circulating pipe is divided into two sections, one section is a circulating pipe I, and the other section is a circulating pipe II. The inlet of the cyclone dust collector branch is connected with an outlet of the circulating pipe I, the air outlet of the cyclone dust collector is connected with an inlet of the circulating pipe II, an inlet of the circulating pipe I is the inlet of the circulating pipe, and other functional branch ports are arranged on the circulating pipe II. Furthermore, preferably, the circulating pipe I and the circulating pipe II are further provided with bypass pipe ports of the cyclone dust collector branch, and a bypass pipe with a bypass valve is arranged between the two bypass pipe ports.

In order to achieve processing of materials requiring operations at normal temperature and shape maintenance, in the circulating fluidized bed apparatus with the molecular sieve dryer branch, the circulating pipe and/or the feeding pipe is further provided with a storage shelf which is used for placing materials needing to be dried, the storage shelf is an airtight box with a door and is internally layered through grids, and the materials are evenly fixed to the grids. Gaps are reserved between the materials, and the sum of the areas of any cross section of the gaps is kept larger than the sectional area of the circulating pipe.

In order to quicken a drying speed, the air outlet of the molecular sieve dryer is further provided with an air heater, and the temperature of hot air output by the air heater is controlled through the regulating device; in order to reduce loss of volatile ingredients in materials, a pipe for feeding to the air outlet the drying medium with high concentration of volatile ingredients at the air inlet of the molecular sieve dryer is further arranged between the air inlet of the molecular sieve dryer and the air outlet, and the sectional area of the pipe is below 60% that of the circulating pipe. Under the conditions that the loss of volatile ingredients is not considered, the circulating pipe may be disconnected with the molecular sieve dryer.

The present invention further provides a circulating fluidized bed system which comprises a front section device and a rear section device which are both composed of the circulating fluidized bed apparatus. A feeding device of the rear section device is a conveying pipe, an inlet of the conveying pipe is connected with an outlet of a discharging valve of the front section device, and an outlet of the conveying pipe is connected with a feeding port of the rear section device.

According to the present invention, one or more circulating channels are formed by sequentially connecting the fan, the circulating pipe, the functional branch and the feeding pipe; the fan and jet stream generated thereby disperse materials into a fluidized state; the fluidized materials circulate and flow at a high speed in the circulating channel to achieve the objectives of the process, efficiently realizing operations such as drying, smashing, evaporating and distilling, concentrating, sieving, mixing, and ultraviolet sterilizing of powdered materials, realizing quick drying at normal temperature, and quickly preparing fresh plant materials into powdered materials at normal temperature. All the operations are performed by one apparatus, thus reducing equipment investment, simplifying production process steps, improving product quality, reducing production costs, and having low energy consumption, wide application and a simple structure. The existing advantages of the Chinese patent 2013107484627 are retained, part of problems of the patent is solved, and the requirements of reducing production costs and improving product quality in relevant industries can be met.

DETAILED DESCRIPTION OF THE INVENTION

The present invention is further described below in combination with drawings and embodiments; however, the embodiments do not lead to limitation to the present invention, and the embodiments are obviously insufficient to completely present all applications of the present invention. Those skilled in the art should understand that various combinations may be performed without departing from the principle of the present invention so as to achieve specific objectives, and various modifications may be performed so as to adapt to different requirements. Thus, the present invention is not limited to the specific embodiments disclosed as below, and comprises all embodiments falling within the scope of the claims.

Embodiment 1: A Circulating Fluidized Bed Air Stream Drying Apparatus

Figure 1:
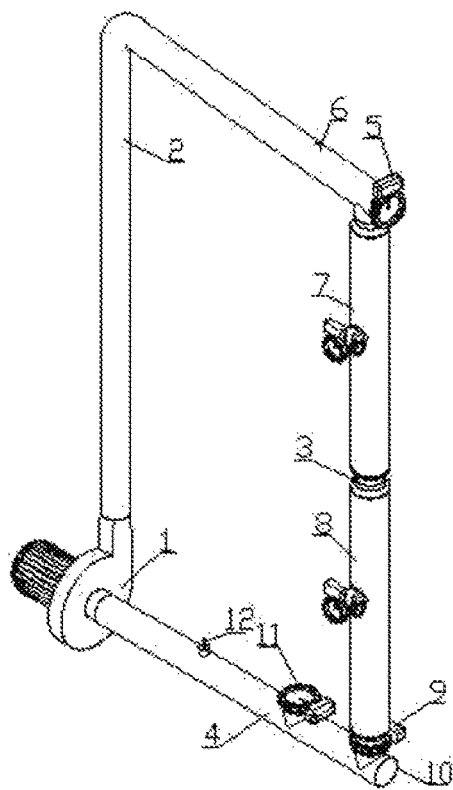
FIG. 1 is a structural drawing of a circulating fluidized bed air stream drying apparatus according to Embodiment 1.

Referring to FIG. 1, a circulating fluidized bed air stream drying apparatus comprises a fan 1, a circulating pipe 2, a bag type dust collector branch 3 and a feeding pipe 4. The circulating pipe 2 is provided with a functional branch port and a discharging port, and a discharging valve 5 is installed on the discharging port. The bag type dust collector branch 3 is formed by sequentially connecting a first bag type dust collector 7, a second bag type dust collector 8 and a regulating valve 9. An inlet of the first bag type dust collector 7 is an inlet of the bag type dust collector branch 3, an outlet of the regulating valve 9 is an outlet of the bag type dust collector branch 3. The head end of the feeding pipe 4 is an air inlet 10 of the apparatus of this embodiment, and the tail end of the feeding pipe 4 is an outlet. The feeding pipe 4 is provided with a functional branch port and two feeding ports, a feeding port is provided with a feeding valve 11, and the other feeding port is provided with an atomizer 12. The aforementioned components are communicated in such a sequence as an air outlet of the fan 1, an inlet of the circulating pipe 2, the functional branch port of the circulating pipe 2, the inlet of the bag type dust collector branch 3, the outlet of the bag type dust collector branch 3, the functional branch port of the feeding pipe 4, the outlet of the feeding pipe 4 and the air inlet of the fan 1 to form a circulating channel. The circulating fluidized bed apparatus in this embodiment is further provided with an inlet air stream temperature regulating device and a fan rotating speed regulating device. The inlet air stream temperature regulating device controls the temperature of inlet air stream through output signals of a temperature sensor 6 installed on the circulating pipe 2; and the fan rotating speed regulating device is used for regulating the rotating speed of the fan so as to control heat produced by converting kinetic energy of the fan, so that the temperature inside the apparatus does not exceed a set temperature. The first bag type dust collector 7 and the second bag type dust collector 8 have the same structure as the bag type dust collector described in the Chinese patent 2013107484627. The apparatus in this embodiment takes the fan and the regulating valve as the boundary, the pressure inside the circulating pipe and the bag type dust collector is positive pressure, and pressure inside the feeding pipe is negative pressure. The structural strength of the fan in this embodiment should meet the use requirements; due to the configurations of a fan motor and a pipe, when the fan performs idle motion under the power supply frequency conditions, the working current of the motor is 10-25% the rated current thereof, and the air speed in the circulating pipe is 30 m/s or above.

The circulating fluidized bed apparatus described in this embodiment has the following functions: 1. Powdered materials are dried and are added into the apparatus through the feeding valve 11, the materials form a fluidized state under the fan and jet stream produced thereof to circulate and flow at a high speed in the circulating channel; heat and moisture exchange is performed quickly between the materials and the air stream; most of air stream in the fluidized materials entering the bag type dust collector branch is separated through the first bag type dust collector 7 and the second bag type dust collector 8 to be discharged out of the apparatus through the air outlet of the bag type dust collector branch, and the air stream takes away moisture produced due to drying; the materials along with a small part of air stream enters the feeding pipe through the regulating valve to be subject to circulation drying, and the quantity of air stream discharged out of the apparatus can be adjusted by adjusting the opening of the regulating valve 9, the drying rate can be adjusted by adjusting the inlet air stream temperature and the rotating speed of the fan, and the materials are discharged out of the discharging valve 5 on the discharging port of the circulating pipe after being dried. 2. Liquid materials are dried, and are added into the apparatus after being atomized into particles through the atomizer 12. 3. Powdered materials are mixed. 4. Powered materials and liquid materials are mixed and the mixture is dried. 5. Heat in air can be utilized in a large scale to achieve air energy drying. The flow velocity of fluidized materials in this embodiment is generally 35 m/s or above, the speed of heat and moisture exchange between the materials and the air stream is very quick, so that room temperature air stream is adopted as inlet air; when the material moisture content is 20% or above, before the materials enter a speed reduction drying period in the drying process, the temperature in the feeding pipe will be lowered to below the environment temperature; at the time, heat for moisture vaporization has three sources, one is heat contained in inlet air stream, another is heat absorbed from the environment by the surface of the apparatus, and the third one is heat produced by converting kinetic energy of the fan. 6. Quick normal temperature drying can be achieved. Since the speed of heat and moisture exchange between materials and air stream is very quick, heat in the inlet air stream is consumed quickly by moisture vaporization, and it is difficult to increase the temperature of fluidized materials; the temperature of the inlet air stream can be controlled through the regulating device to control the temperature in the circulating pipe to be below 50 degrees centigrade; after the temperature of the inlet air stream is lowered to room temperature, the content of moisture in the materials has been reduced greatly at the time, effective circulation of the materials can be guaranteed without needing a very high air speed, the rotating speed of the fan can be reduced through the regulating device to reduce heat produced by converting kinetic energy of the fan, so as to control the temperature in the circulating pipe to be below 50 degrees centigrade. 7. The apparatus can be used for smashing low-hardness lump materials and small-particle materials; by appropriate material selection, fan impellers can bear impact of the low-hardness lump materials such as plant materials and small-particle hard mineral materials with the particle sizes of below 100 microns; the materials circulating and flowing at a high speed are smashed under effects of fan impellers, the pipe wall and mutual impact, and the smashing speed and the particle sizes of the obtained materials can be regulated by changing the rotating speed of the fan through the fan rotating speed regulating device. 8. Due to the functions in the aforementioned items 5 and 6, the energy consumption of the whole circulating fluidized bed apparatus for drying operations in this embodiment can be lowered to below 2800 kj/kg(H2O). 9. By mounting the ultraviolet sterilization lamp tube in the circulating channel according to the method described in the Chinese patent 2013107484627, this embodiment can be used for ultraviolet sterilization of powdered materials.

Embodiment 2: A Circulating Fluidized Bed Air Stream Screening Apparatus

Figure 2:
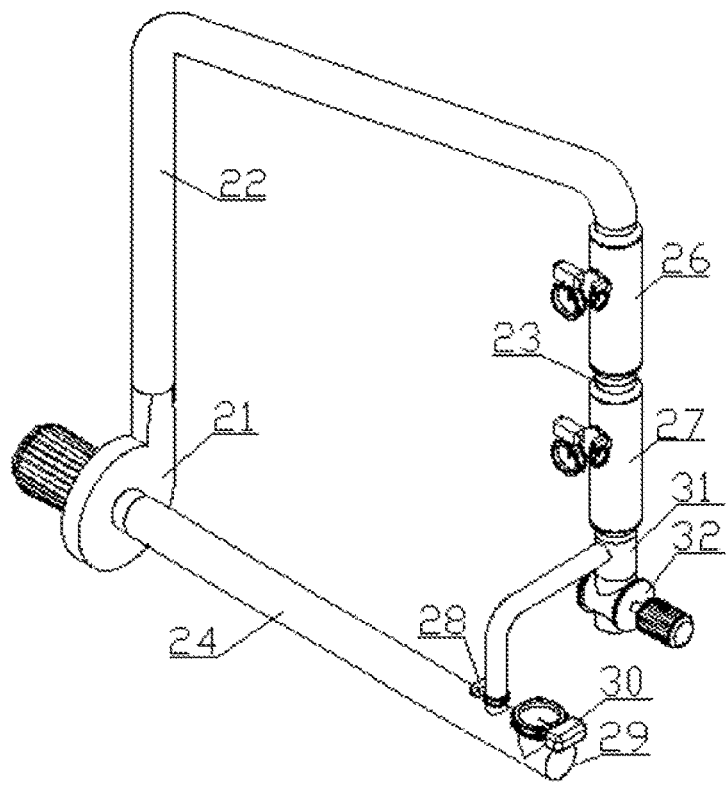
FIG. 2 is a structural drawing of a circulating fluidized bed air stream screening apparatus according to Embodiment 2.
Figure 20:
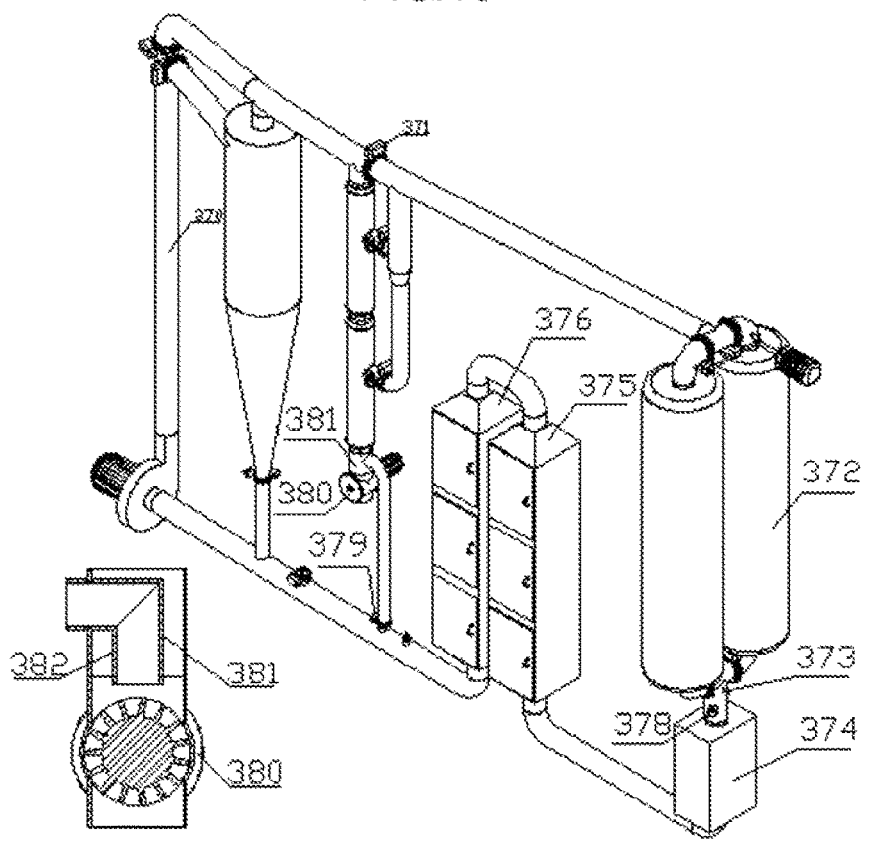
FIG. 20 is a structural drawing of a multi-purpose circulating fluidized bed apparatus with a molecular sieve dryer branch and a connection diagram of a discharging tee with a bend and a planet discharging valve according to Embodiment 17.

Referring to FIG. 2, a circulating fluidized bed air stream screening apparatus comprises a fan 21, a circulating pipe 22, a screen drum branch 23 and a feeding pipe 24. The circulating pipe 22 is provided with a functional branch port, and the screen drum branch 23 is formed by sequentially connecting a first screen drum 26, a second screen drum 27, a slag-discharging tee 31 and a regulating valve 28. An inlet of the first screen drum 26 is an inlet of the screen drum branch, an outlet of the regulating valve 28 is an outlet of the screen drum branch, an inlet of the slag-discharging tee 31 is connected with an ash-discharging port of the second screen drum, a second port of the slag-discharging tee 31 is provided with a planet discharging valve 32, and the regulating valve 28 is arranged on a third port of the slag-discharging tee 31. A bend (referring to FIG. 20) is arranged in the slag-discharging tee 31, one end of the bend is connected with the third port in the slag-discharging tee 31, and the other end of the bend is arranged in the second port in a suspended mode. Materials collected by the screen drum branch are discharged through the planet discharging valve 32. The head end of the feeding pipe 24 is an air inlet 29 of the circulating fluidized bed air stream screening apparatus, and the tail end of the feeding pipe 24 is an outlet. The feeding pipe 24 is provided with a functional branch port and a feeding port, and a feeding valve is positioned on the feeding port. The aforementioned components are communicated in such a sequence as an air outlet of the fan 21, an inlet of the circulating pipe 22, the functional branch port of the circulating pipe 22, the inlet of the screen drum branch, the outlet of the screen drum branch, the functional branch port of the feeding pipe 24, an outlet of the feeding pipe 24 and an air inlet of the fan 21 to form a circulating channel. The first screen drum 26 and the second screen drum 27 have the same structure as the screen drum described in the Chinese patent 2013107484627.

One suspended end of the bend in the slag-discharging tee is close to the inlet of the planet discharging valve. Since it is negative pressure in the feeding pipe, during normal circulation screening, the planet discharging valve is switched off, the regulating valve is switched on, materials falling into the bottom of the screen drum branch are sucked out to enter the feeding pipe; after the screening is finished, the planet discharging valve is switched on, the regulating valve is switched off, and oversize products are discharged through the planet discharging valve.

The circulating fluidized bed air stream screening apparatus in this embodiment is used for performing meshed air stream screening and superfine grinding on powdered materials and can control the upper limit of the particle size of screen underflow accurately; when the circulating fluidized bed air stream screening apparatus is used for superfine grinding, since materials with the particle sizes conforming to the requirements are discharged timely, the efficiency is improved compared with the situation that the circulating fluidized bed air stream drying apparatus is used for smashing operation.

Embodiment 3: A Circulating Fluidized Bed Grinding Apparatus

Figure 3:
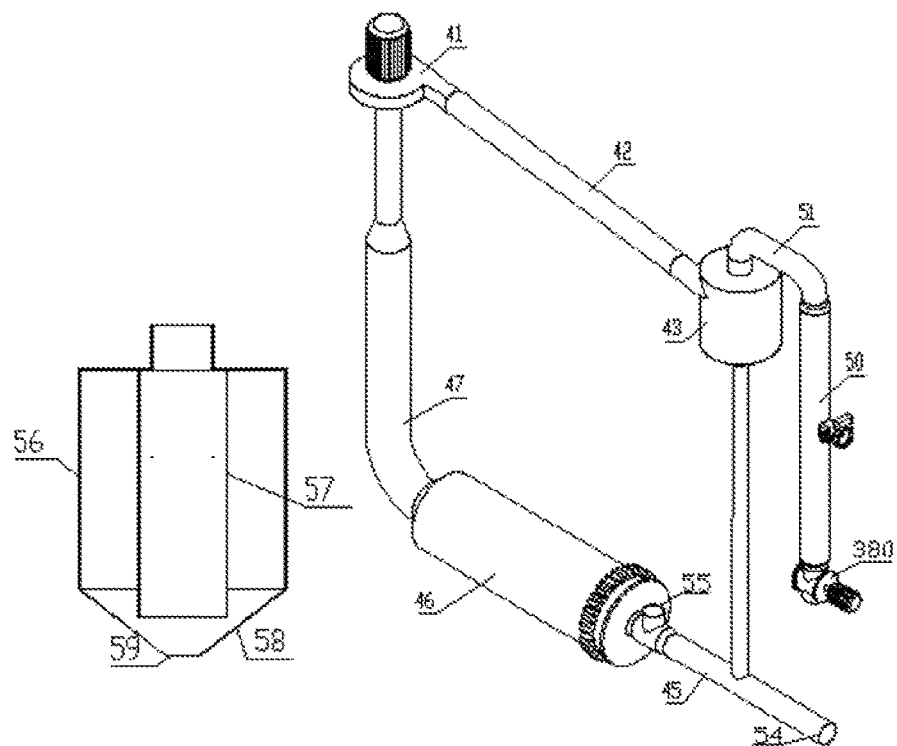
FIG. 3 is a structural drawing of a circulating fluidized bed grinding apparatus and a structural drawing of a cyclone dust collector for material classification according to Embodiment 3.

Referring to FIG. 3, in this embodiment, the circulating fluidized bed grinding apparatus comprises a fan 41, a circulating pipe I 42, a cyclone dust collector branch 43, a feeding pipe 45, a mill 46, a feeding pipe rear section 47, a circulating pipe II 51 and a bag type dust collector branch. The cyclone dust collector branch 43 is composed of a cyclone dust collector used for material classification, the ratio of the diameter of a barrel 56 to the height of a cone 58 is 2.2, and a separating drum 57 for separating low vortex air stream and upper vortex air stream is arranged in the barrel 56. The upper end of the separating drum 57 is connected with an upper end cover of a cyclone dust collector, the lower end of the separating drum 57 extends into the cone 58, and the particle size of fine powder separated out of the cyclone dust collector can be adjusted by adjusting the diameter of the separating drum 57 and the distance between the lower end face of the separating drum 57 and the cone 58. An air inlet of the cyclone dust collector is an inlet of the cyclone dust collector branch 43, an ash discharging port of the cyclone dust collector is an outlet of the cyclone dust collector branch 43, and an air outlet of the cyclone dust collector is an air outlet of the cyclone dust collector branch 43. A feeding pipe is provide with a feeding port 55 and a cyclone dust collector branch port, the feeding port is close to the air outlet, the mill 46 is formed by omitting a comb mesh based on a common mill, the feeding pipe rear section 47 is vertically arranged and is a variable diameter pipe, and the pipe diameter of the inlet end is larger than that of the outlet end. The aforementioned components are communicated in such a sequence as an outlet of the fan 41, an inlet of the positive pressure circulating pipe I 42, an outlet of the positive pressure circulating pipe I 42, an air inlet of the cyclone dust collector branch 43, the outlet of the cyclone dust collector branch, the cyclone dust collector branch port on the feeding pipe 45, the outlet of the feeding pipe 45, a feeding port of the mill 46, a discharging port of the mill 46, an inlet of the feeding pipe rear section 47, an outlet of the feeding pipe rear section 47 and an inlet of the fan 41 to form a circulating channel. A bag type dust collector branch is composed of a bag type dust collector 50 and a planet discharging valve 380, the bag type dust collector 50 has the same structure as the bag type dust collector in Embodiment 1, an outlet of the bag type dust collector 50 is connected with an inlet of the planet discharging valve 380, and an outlet of the planet discharging valve 380 is a discharging port in this embodiment. An inlet of the bag type dust collector branch is connected with an outlet of the positive pressure circulating pipe II 51, and an inlet of the positive pressure circulating pipe II 51 is connected with an air outlet of the cyclone dust collector branch 43.

In this embodiment, by making the mill be in series connection with the feeding pipe of the circulating fluidized bed technology apparatus, the mill is utilized to smash chunk hard materials, powdered materials made by the mill form a fluidized state under the effect of the fan and enter the fan along with the air stream to be ground once again under the impact effect of fan impellers; after the fluidized materials enter the cyclone dust collector, qualified fine powder enters the bag type dust collector branch through the circulating pipe II to be separated out of the fluidized materials and fall into the bottom of the bag type dust collector to be discharged through the planet discharging valve, unqualified powdered materials enter the feeding pipe through the ash discharging port of the cyclone dust collector to be ground once again; since the fine powder made by the mill is separated timely, the grinding efficiency is improved, and the energy consumption in grinding operation is reduced; the cyclone dust collector branch serves as a powder selection device, the structure of the cyclone dust collector branch is simpler than that of a common powder selection device, the equipment cost is low, and the problem that the circulating fluidized bed technology apparatus in Embodiment 1 cannot be used for smashing chunk mineral hard materials is solved.

Figure 4:
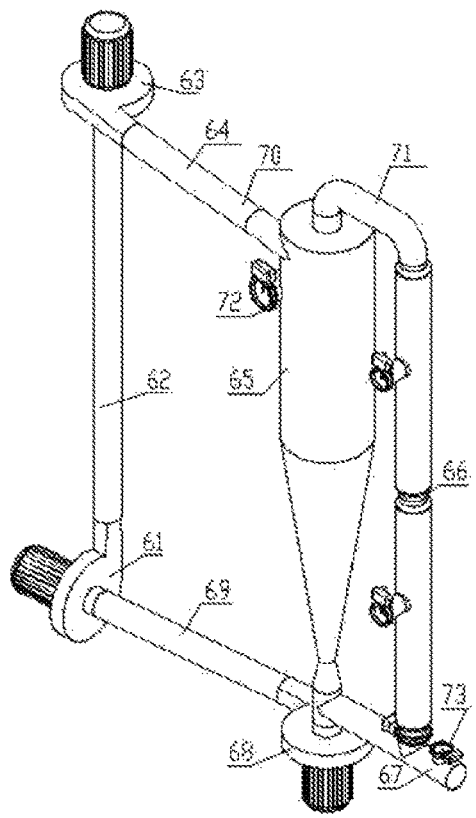
FIG. 4 is a structural drawing of a circulating fluidized bed air stream drying apparatus for processing high-humidity high-viscosity materials according to Embodiment 4.
Figure 5:
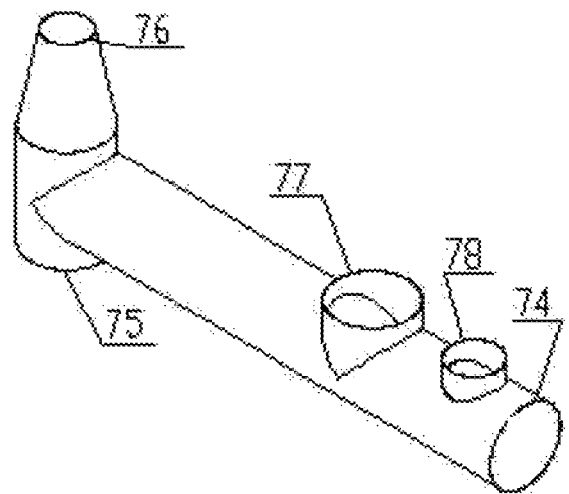
FIG. 5 is a structural drawing of a feeding pipe in Embodiment 4.

Embodiment 4: A Circulating Fluidized Bed Air Stream Drying Apparatus for Processing High-Humidity High-Viscosity Materials Referring to FIGS. 4 and 5, the circulating fluidized bed air stream drying apparatus for processing the high-humidity high-viscosity material is composed of a fan 61, a circulating pipe front section 62, a second fan 63, a circulating pipe 64, a cyclone dust collector branch 65, a bag type dust collector branch 66, a feeding pipe 67, a third fan 68 and a feeding pipe rear section 69. The circulating pipe 64 comprises a circulating pipe I 70 and a circulating pipe II 71. An inlet of the circulating pipe I 70 is an inlet of the circulating pipe 64, and an outlet of the circulating pipe II 71 is a port of the bag type dust collector branch 66. The cyclone dust collector branch 65 is composed of a cyclone dust collector used for material-gas separation. The sectional area of an ash discharging port of the cyclone dust collector is one-tenth that of an air inlet, and the cyclone dust collector is further provided with a discharging port which is provided with a discharging valve 72. The air inlet of the cyclone dust collector is an inlet of the cyclone dust collector branch 65, the ash discharging port of the cyclone dust collector is an outlet of the cyclone dust collector branch 65, an air outlet of the cyclone dust collector is an air outlet of the cyclone dust collector branch 65, the inlet of the cyclone dust collector branch 65 is connected with an outlet of the circulating pipe I 70, the air outlet of the cyclone dust collector branch 65 is connected with an inlet of the circulating pipe II 71. The bag type dust collector branch 66 has the same structure as the bag type dust collector branch in Embodiment 1, and the inlet of the bag type dust collector branch 66 is connected with the port of the bag type dust collector branch 66 on the circulating pipe II 71. The head end of the feeding pipe 67 is an air inlet 74 of the apparatus in this embodiment, the tail end of the feeding pipe 67 is an outlet 75, and the feeding pipe 67 is provided with a port 76 of the cyclone dust collector branch 65, a port 77 of the bag type dust collector branch 66 and a feeding port 78. The feeding port 78 is provided with a feeding valve 73, the port 76 of the cyclone dust collector branch 65 on the feeding pipe 67 is connected with the outlet of the cyclone dust collector branch 65, the port of the bag type dust collector branch 66 is connected with the outlet of the bag type dust collector branch 66, the outlet 75 of the feeding pipe 67 is connected with an air inlet of the third fan 68, an air outlet of the third fan 68 is connected with an inlet of the feeding pipe rear section 69, an outlet of the feeding pipe rear section 69 is connected with the air inlet of the fan 61, an air outlet of the fan 61 is connected with an inlet of the circulating pipe front section 62, an outlet of the circulating pipe front section 62 is connected with an air inlet of the second fan 63, and an air outlet of the second fan 63 is connected with the inlet of the circulating pipe 64.

When the circulating fluidized bed apparatus in Embodiment 1 is used for processing the high-humidity high-viscosity materials, the shortcoming that the materials will be attached to the turning of the circulating channel and a dust collector filter material occurs. According to this embodiment, on one hand, the problem that the materials are attached to the turning is solved by arranging the fan at the turning of the circulating channel, on the other hand, by utilizing the cyclone dust collector to perform primary material-gas separation so that the high-humidity high-viscosity materials no longer enter the bag type dust collector branch, the problem that the viscous materials are attached to the dust collector filter material is solved, and the circulating fluidized bed apparatus is suitable for drying the high-humidity high-viscosity materials and drying and grinding of fresh plant materials.

Figure 6:
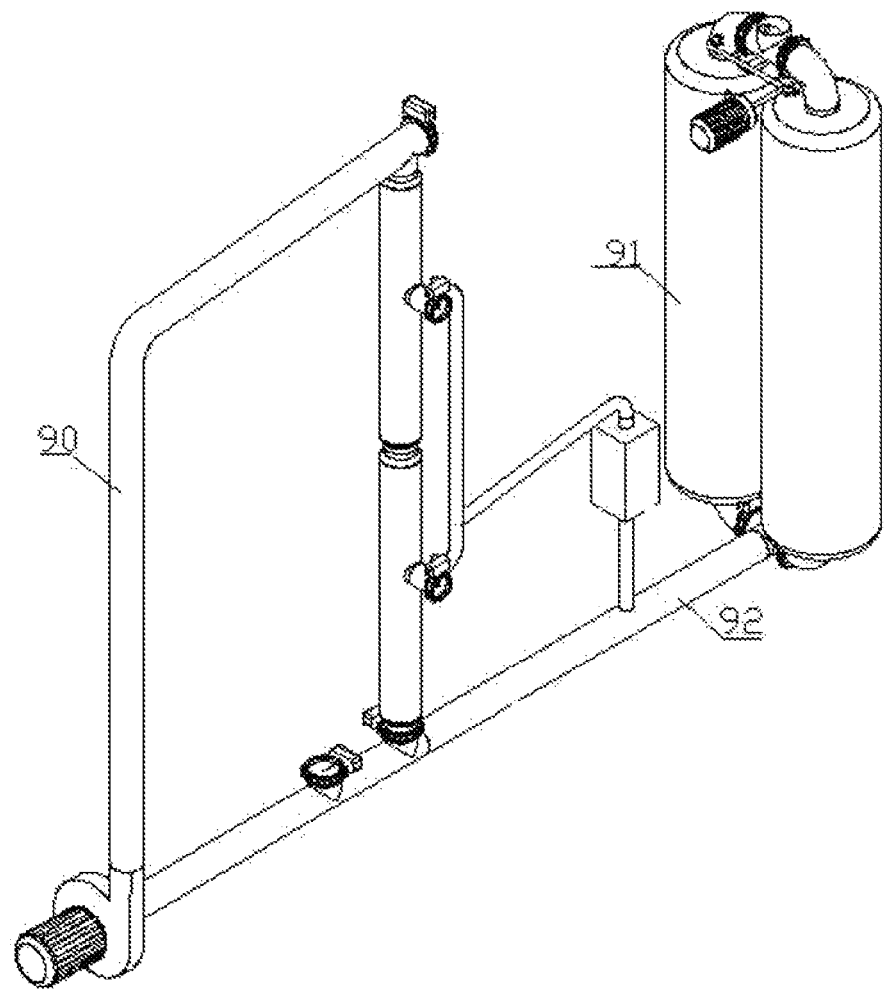
FIG. 6 is a structural drawing of a circulating fluidized bed apparatus with an inlet gas treatment device according to Embodiment 6.
Figure 7:
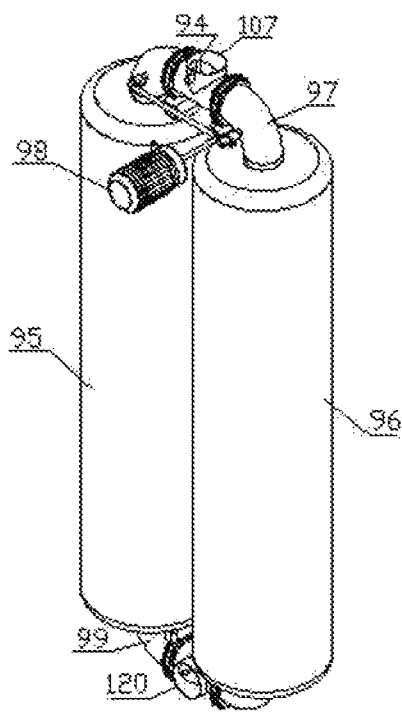
FIG. 7 is a structural drawing of a molecular sieve dryer embodiment.

Embodiment 5: A Circulating Fluidized Bed Air Stream Drying Apparatus for Drying Materials which Cannot be Pumped and are Difficult to Disperse In this embodiment, the circulating fluidized bed air stream drying apparatus is formed by using an extruding machine to replace a feeding valve 73 based on Embodiment 4. The extruding machine can extrude materials similar to plasticine which are difficult to disperse and cannot be pumped into lines and add the lines into the feeding pipe to achieve circulating air stream drying, and the discharging port of the extruding machine is connected with the feeding port 78 on the feeding pipe 67 of the circulating fluidized bed air stream drying apparatus for processing high-humidity high-viscosity materials in Embodiment 4;

Embodiment 6: A Circulating Fluidized Bed Apparatus with an Inlet Gas Treatment Device Referring to FIGS. 6 and 7, in this embodiment, the circulating fluidized bed apparatus is formed by arranging a molecular sieve dryer serving as an inlet gas treatment device on the air inlet of the circulating fluidized bed air stream drying apparatus. The circulating fluidized bed apparatus in this embodiment is composed of a circulating fluidized bed apparatus 90, a molecular sieve dryer 91 and a supply air duct 92 in Embodiment 1, and the molecular sieve dryer 91 is the molecular sieve dryer in the background technology. The molecular sieve dryer 91 is connected with an air inlet of the circulating fluidized bed apparatus 90 in Embodiment 1 through the supply air duct 92, the supply air duct 92 is further provided with a branch pipe for feeding gas to a blowback air source supercharging device, and an air inlet of the molecular sieve dryer is communicated with air outside the apparatus.

A molecular sieve in the molecular sieve dryer in this embodiment is a molecular sieve having an oxygen adsorption effect. In this embodiment, by reducing oxygen content in inlet air stream, the problem of material oxidization occurring when the circulating fluidized bed apparatus is used for processing easily-oxidized materials and the problem of dust explosion hidden danger occurring when the circulating fluidized bed apparatus is used for processing combustible materials in Embodiment 1 are solved, low oxygen content inlet gas conforming to the process requirements is supplied through the apparatus, and is good in economy compared with outsourcing.

Figure 8:
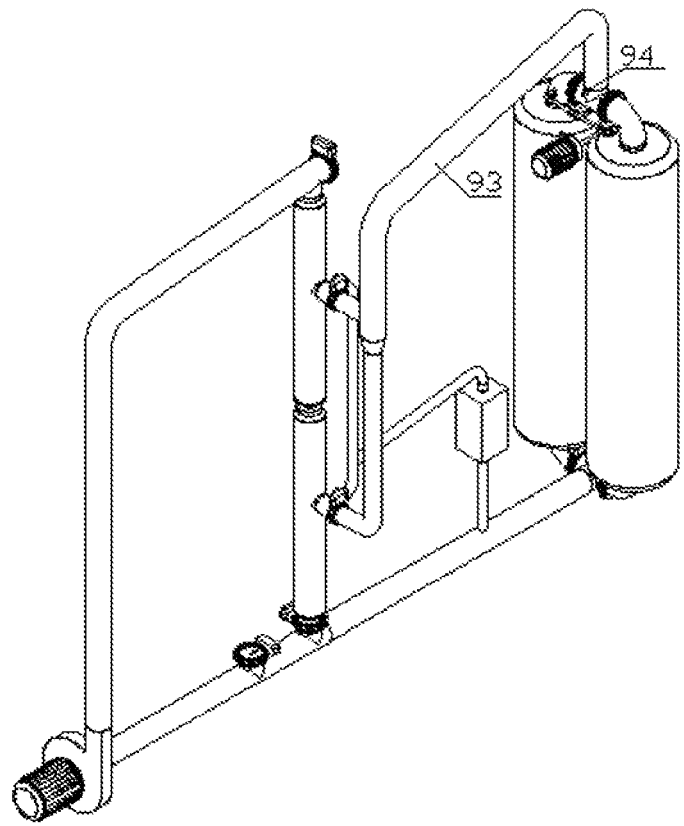
FIG. 8 is a structural drawing of another circulating fluidized bed apparatus with an inlet gas treatment device according to Embodiment 7.

Embodiment 7: Another Circulating Fluidized Bed Apparatus with an Inlet Gas Treatment Device Referring to FIG. 8, in this embodiment, the circulating fluidized bed apparatus is formed by adding an inlet air pipe 93 for conveying to the molecular sieve dryer the exhaust discharged out of the bag type dust collector branch based on the circulating fluidized bed apparatus with the inlet gas treatment device in Embodiment 6. A tee of an inlet air pipe of the molecular sieve dryer is provided with a gas supply port 94 which is communicated with natural air outside the apparatus, and a molecular sieve in the molecular sieve dryer is composed of a molecular sieve having a water adsorption effect and a molecular sieve having an oxygen adsorption effect according to a weight ratio of 9:1. Compared with the apparatus in Embodiment 6, the apparatus in this embodiment greatly reduces the quantity of gas entering the apparatus from the outside, so that pollution led in by the inlet air stream is greatly reduced; at the same time, the temperature of exhaust is generally higher than that of gas outside the apparatus, the water content of gas output by the inlet gas treatment device is lower than that of natural air; when the apparatus is used for drying, the drying speed is quicker, and the apparatus has a certain energy saving effect; when the apparatus is used for drying materials with volatile ingredients, such as maca, due to the fact that a drying medium does not leak much, the concentration of volatile ingredients in the drying medium is increased after the volatile ingredients are volatilized, the saturation deficit of the volatile ingredients is reduced, the effect of restraining volatilization of the volatile ingredients can be achieved, and the loss of the volatile ingredients in materials, such as glucosinolate in maca, is reduced to some extent.

Figure 9:
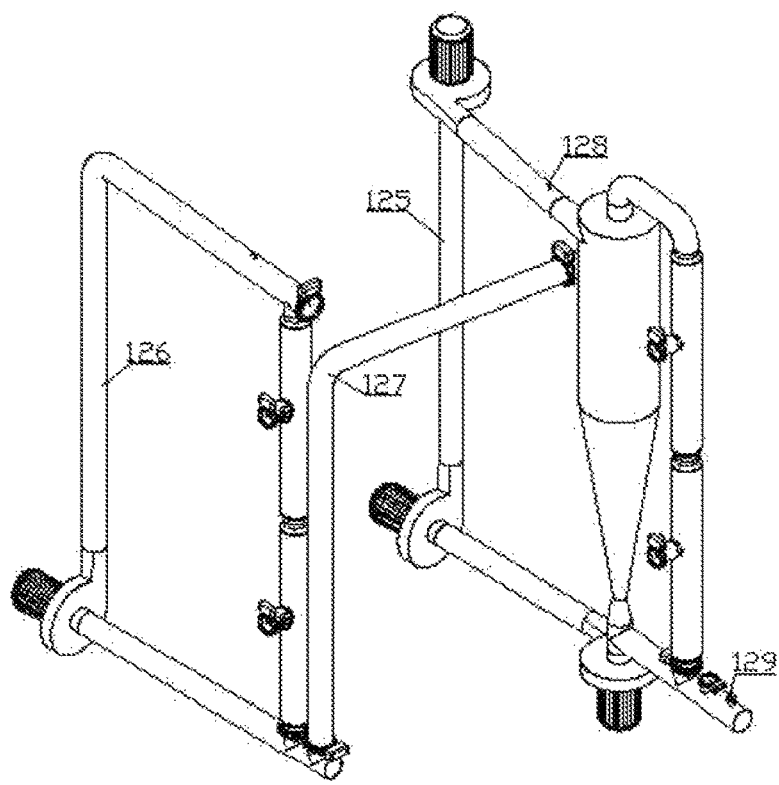
FIG. 9 is a structural drawing of a circulating fluidized bed normal-temperature air stream drying apparatus for processing high-humidity high-viscosity materials according to Embodiment 8.

Embodiment 8: A Circulating Fluidized Bed Normal-Temperature Air Stream Drying Apparatus for Processing High-Humidity High-Viscosity Materials Referring to FIG. 9, the circulating fluidized bed normal-temperature air stream drying apparatus for processing high-humidity high-viscosity materials is composed of a front section device 125, a rear section device 126 and a conveying pipe 127. The front section device 125 is formed by adding an atomizer 129 arranged on another feeding port of the feeding pipe and a regulating device based on the circulating fluidized bed air stream drying apparatus for processing high-humidity high-viscosity materials in Embodiment 4. The regulating device comprises an inlet air stream temperature regulating device and a fan rotating speed regulating device. The inlet air stream temperature regulating device controls the temperature of inlet air stream through output signals of a temperature sensor 128 installed on the circulating pipe, so that the temperature inside the apparatus does not exceed a set temperature; and the fan rotating speed regulating device is used for regulating the rotating speed of the fan so as to control heat produced by converting kinetic energy of the fan, so that the temperature inside the apparatus does not exceed a set temperature. The rear section device 126 is formed by omitting the atomizer based on the circulating fluidized bed apparatus in Embodiment 1. A feeding device of the rear section device is the conveying pipe 127, an inlet of the conveying pipe 127 is connected with an outlet of a discharging valve of the front section device, and an outlet of the conveying pipe 127 is connected with a feeding port of a rear section dryer.

Fresh medicine plant materials such as dendrobium nobile, maca and panax notoginseng and liquid materials obtained by squeezing fresh plant, such as barley seedling juice, need to be dried quickly at a normal temperature state to a set degree. Though the circulating fluidized bed air stream drying apparatus for processing high-humidity high-viscosity materials is quick in drying speed, the influence that fluidized materials are compressed to lead to the temperature rise in the circulating pipe cannot be neglected since multiple fans are in series connection; at a speed reduction drying stage, the method of lowering inlet air stream temperature and reducing the rotating speed of the fan so as to control the temperature in the apparatus will be invalid. In this embodiment, when the temperature control in the apparatus fails and the temperature in the apparatus approaches the set temperature, materials in a front section dryer can be discharged into a rear section dryer through the conveying pipe 127 to continue being dried, and the problem that the pressure in the circulating pipe rises to lead to temperature rise, so that it has an adverse effect on temperature control over the fluidized materials is solved.

Figure 10:
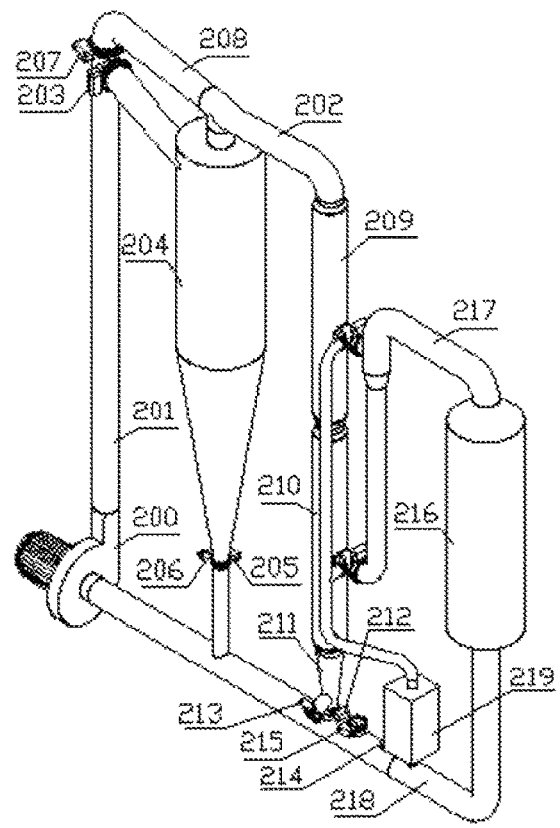
FIG. 10 is a structural drawing of a closed loop circulating fluidized bed distillation apparatus according to Embodiment 9.

Embodiment 9: A Closed Loop Circulating Fluidized Bed Drying and Distillation Apparatus Referring to FIG. 10, the closed loop circulating fluidized bed drying and distillation apparatus is composed of a circulating fluidized bed drying and evaporation apparatus and an exhaust treatment device 216. The circulating fluidized bed drying and evaporation apparatus is composed of a fan 200, a circulating pipe, a cyclone dust collector branch, a bypass pipe 208, a bag type dust collector branch and a feeding pipe. The circulating pipe is composed of a circulating pipe I 201 and a circulating pipe II 202. The head end of the circulating pipe I 201 is an inlet of the circulating pipe, and the circulating pipe I 201 is further provided with a bypass pipe port and an outlet; the head end of the circulating pipe II 202 is an inlet, and an outlet is a bag type dust collector branch port. The circulating pipe II 202 is further provided with a bypass pipe port. The cyclone dust collector branch is formed by sequentially connecting an inlet valve 203, a cyclone dust collector 204 and an ash discharging valve 205 mounted on an ash discharging port of the cyclone dust collector. The position of a cone of the cyclone dust collector 204 close to the ash discharging port is further provided with a discharging port which is provided with a discharging valve 206, and the sectional area of the ash discharging port of the cyclone dust collector 204 is one-sixth that of the air outlet. An inlet of the inlet valve 203 is an inlet of the cyclone dust collector branch, an outlet of the ash discharging valve 205 is an outlet of the cyclone dust collector branch, and an air outlet of the cyclone dust collector 204 is an air outlet of the cyclone dust collector branch. An inlet of the cyclone dust collector branch is connected with an outlet of the circulating pipe I 201 and an air outlet of the cyclone dust collector branch is connected with an inlet of the circulating pipe II 202. The bypass pipe is composed of a bypass pipe 208 and a valve 207 arranged on the bypass pipe 208, and the bypass pipe is connected between the bypass pipe port positioned on the circulating pipe I 201 and the bypass pipe port positioned on the circulating pipe II 202. The bag type dust collector branch is formed by sequentially connecting a first bag type dust collector 209, a second bag type dust collector 210, a discharging tee 211 and a regulating valve 212. The first bag type dust collector 209 and the second bag type dust collector 210 are the same as the bag type dust collector in Embodiment 1. A third port of the discharging tee 211 is provided with a discharging valve 213. An inlet of the first bag type dust collector 209 is an inlet of the bag type dust collector branch, and an outlet of the regulating valve 212 is an outlet of the bag type dust collector branch. The inlet of the bag type dust collector branch is connected with the bag type dust collector branch port on the circulating pipe II 202. The head end of the feeding pipe is an air inlet of the circulating fluidized bed drying and evaporation apparatus, the tail end of the feeding pipe is an outlet, and from the head end, the feeding pipe is sequentially provided with a bag type dust collector branch port and a cyclone dust collector branch port. The bag type dust collector branch port is connected with the outlet of the bag type dust collector branch, the cyclone dust collector branch port is connected with the outlet of the cyclone dust collector branch, the feeding pipe is further provided with two feeding ports, a feeding device on one feeding port is an atomizer 214, and a feeding device on the other feeding port is a feeding valve 215. The outlet of the feeding pipe is connected with the air inlet of the fan 200, and the air outlet of the fan is connected with the inlet of the circulating pipe. The exhaust treatment device 216 is a condenser or a device for collecting special ingredients, the inlet of the exhaust treatment device 216 is connected with the air outlet of the bag type dust collector branch through a pipe 217, and the outlet of the exhaust treatment device 216 is connected with the air inlet of the circulating fluidized bed drying and evaporation apparatus and a blowback air source supercharging device 219 through a supply air duct 218.

In the apparatus in this embodiment, the cyclone dust collector branch serves as a primary material-gas separation device to pre-separate wet materials attached to a dust collector filter material, so that the problem that the wet materials are attached to the dust collector filter material is solved. The apparatus can be used for preparation of volatile ingredients in solid materials and liquid materials, such as fermented grain distillation, crude distillation and preparation of fresh water from seawater. Due to the fact that the inside of the apparatus is completely isolated from the outside of the apparatus, volatile ingredients are not lost, processed materials are not subject to atmospheric pollution, and no environmental pollution is caused, and after operations are finished, material slag in the apparatus can be discharged out of the discharging valve on the cyclone dust collector according to material properties and can also be discharged out of the discharging valve on a discharging tee of the bag type dust collector branch. In this embodiment, the apparatus not only has the advantages of the circulating fluidized bed apparatus in Embodiment 1, but also can be used for many operation occasions where there are strict requirements.

Figure 11:
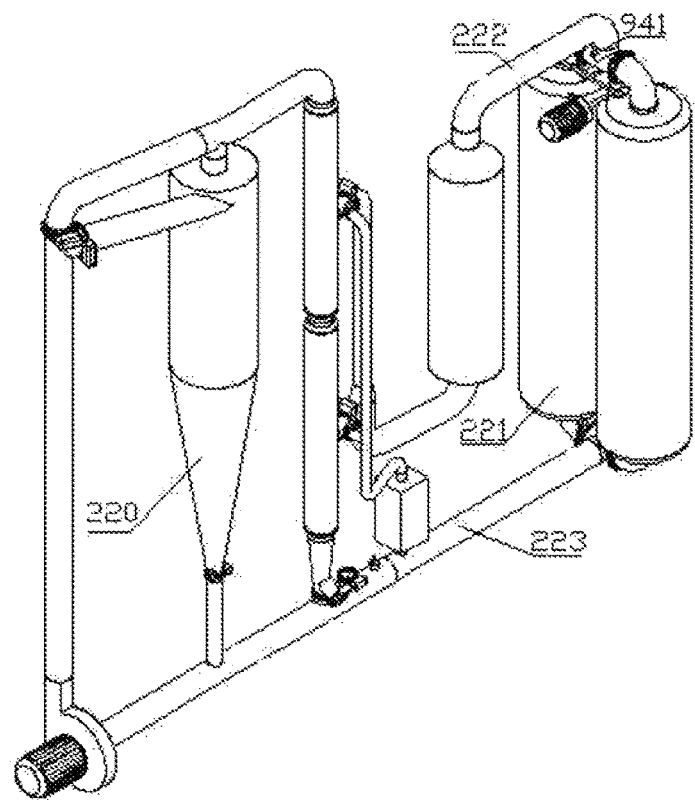
FIG. 11 is a structural drawing of a closed loop circulating fluidized bed air stream drying apparatus with an inlet gas treatment device according to Embodiment 10.

Embodiment 10: A Closed Loop Circulating Fluidized Bed Air Stream Drying Apparatus with an Inlet Gas Treatment Device Referring to FIG. 11, the closed loop circulating fluidized bed air stream drying apparatus with the inlet gas treatment device is formed by adding a molecular sieve dryer based on the apparatus in Embodiment 9. The closed loop circulating fluidized bed air stream drying apparatus is composed of a closed loop circulating fluidized bed distillation apparatus 220 and a molecular sieve dryer 221. An air inlet of the molecular sieve dryer 221 is connected with an air outlet of an exhaust treatment device through an inlet air pipe 222, and an air outlet of the molecular sieve dryer 221 is connected with an air inlet of the closed loop circulating fluidized bed distillation apparatus 220 and a blowback air source supercharging device through a supply air duct 223. An inlet of the inlet air pipe of the molecular sieve dryer 221 is provided with a gas supply port 941 which is communicated with an inert gas source, and a molecular sieve in the molecular sieve dryer 221 is a molecular sieve having a water adsorption effect.

In the apparatus in this embodiment, moisture in high-humidity exhaust and/or volatile ingredients volatilized from materials are condensed and separated through the exhaust treatment device, and gas discharged by the exhaust treatment device is supplied to an inlet gas treatment device to undergo deep separation of moisture therein and then serves as inlet air stream. The content of oxygen and the content of water in the inlet air stream are very low, the evaporation rate of moisture in the materials is quicker, the apparatus is suitable for operations such as drying of easily-oxidized and combustible materials and mixing of the materials with liquid materials and can also be used for recycling volatile ingredients in materials, such as glucosinolate, through the exhaust treatment device while directly drying and smashing fresh plant materials such as maca to make powdered materials; the exhaust treatment device is made to stop working; due to the fact that an operation medium does not leak, the apparatus can greatly reduce loss of beneficial volatile ingredients such as glucosinolate in materials while making fresh medicine and food materials such as maca into powdered materials, excipients needing to be added for preforming are added through a feeding valve or an atomizer; all process operations, from drying of fresh medicine and food materials such as fresh maca, power grinding, excipient adding and mixing and the like to mixture preparation before dry granulation can be finished in one time, and the loss of active ingredients is reduced to the maximum extent.

Figure 12:
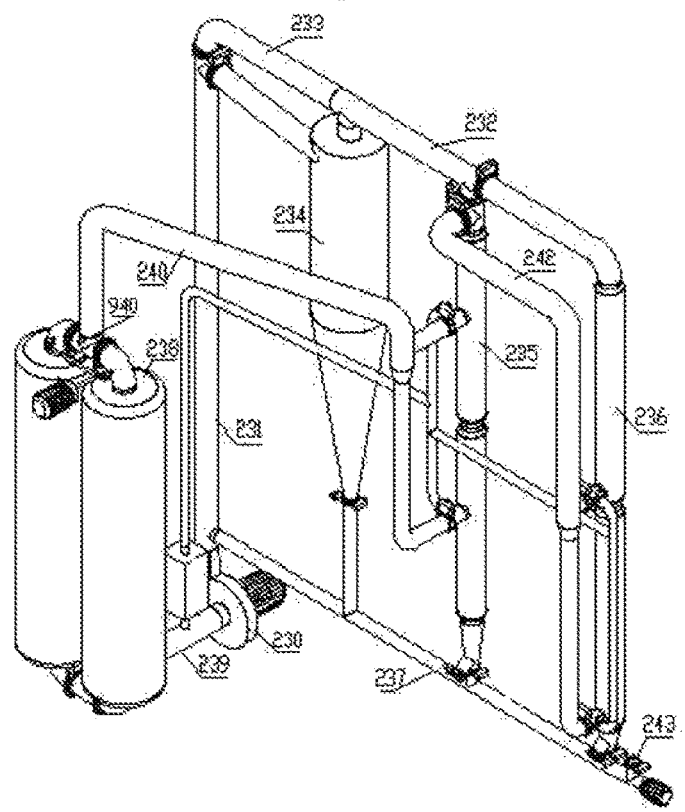
FIG. 12 is a structural drawing of a positive pressure circulating fluidized bed pollen pini processing apparatus according to Embodiment 11.
Figure 13:
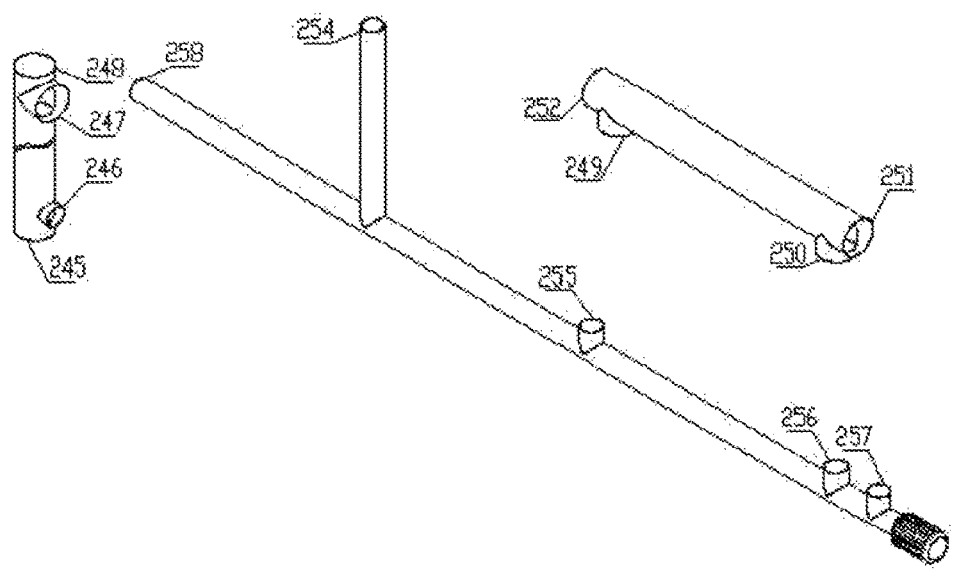
FIG. 13 is a structural drawing of part of components in Embodiment 11.

Embodiment 11: A Positive Pressure Circulating Fluidized Bed Pollen Pini Processing Apparatus Referring to FIGS. 12 and 13, the positive pressure circulating fluidized bed pollen pini processing apparatus is composed of a fan 230, a circulating pipe, a cyclone dust collector branch 234, a bypass pipe 233, a bag type dust collector branch 235, a screen drum branch 236, a conveying pipe 242, a screw conveyor 237 and an inlet gas treatment device 238. The circulating pipe is composed of a circulating pipe I 231 and a circulating pipe II 232. The head end of the circulating pipe I 231 is an inlet 245 of the circulating pipe, a feeding port 246 is further arranged on the circulating pipe I 231 close to the inlet 245, the circulating pipe I 231 is further provided with a cyclone dust collector branch bypass pipe port 248 and an outlet 247; the head end of the circulating pipe II 232 is an inlet 249, and the circulating pipe II 232 is provided with a bag type dust collector branch port 250, a screen drum branch port 251 and a cyclone dust collector branch bypass pipe port 252. The cyclone dust collector branch 234 and the bypass pipe 233 have the same structure as the cyclone dust collector branch and the bypass pipe in Embodiment 10. An inlet of the cyclone dust collector branch 234 is connected with the outlet 247 of the circulating pipe I 231, an air outlet of the cyclone dust collector branch 234 is connected with the inlet 249 of the circulating pipe II 232, and the bypass pipe is connected between the cyclone dust collector branch bypass pipe port 248 on the circulating pipe I 231 and the cyclone dust collector branch bypass pipe port 252 on the circulating pipe II 232. The bag type dust collector branch 235 is formed by sequentially connecting an inlet valve, a conveying tee, a first bag type dust collector, a second bag type dust collector, a discharging tee and a regulating valve. An inlet of the inlet valve is an inlet of the bag type dust collector branch 235, a third port of the conveying tee is provided with a conveying valve, a third port of the discharging tee is provided with a discharging valve, and an outlet of the regulating valve is an outlet of the bag type dust collector branch 235. The first bag type dust collector and the second bag type dust collector have the same structure as the bag type dust collector in Embodiment 1. An air outlet of the first bag type dust collector and an air outlet of the second bag type dust collector are air outlets of the bag type dust collector branch 235, and the inlet of the bag type dust collector branch 235 is connected with the bag type dust collector branch port 250 on the circulating pipe II 232. The screen drum branch 236 is formed by sequentially connecting an inlet valve, a first screen drum, a second screen drum, a slag-discharging tee and a regulating valve. An inlet of the inlet valve is an inlet of the screen drum branch 236, a third port of the slag-discharging tee is provided with a slag-discharging valve, an outlet of the regulating valve is an outlet of the screen drum branch 236, and the first screen drum and the second screen drum have the same structure as the screen drum in Embodiment 2. An air outlet of the first screen drum and an air outlet of the second screen drum are air outlets of the screen drum branch 236. The inlet of the screen drum branch 236 is connected with the screen drum branch port 251 on the circulating pipe II 232, the conveying pipe 242 is further disposed between the air outlet of the screen drum branch 236 and the inlet of the conveying valve of the bag type dust collector branch 235, and the conveying pipe 242 is used for feeding to the bag type dust collector branch 235 the materials discharged out of the screen drum branch 236. The tail end of the conveying pipe of the screw conveyor 237 is a discharging port 258, and from the discharging port, the conveying pipe of the screw conveyor 237 is further sequentially provided with a cyclone dust collector branch port 254, a bag type dust collector branch port 255, a screen drum branch port 256 and a feeding port 257. The cyclone dust collector branch port 254 is connected with the outlet of the cyclone dust collector branch 234, the bag type dust collector branch port 255 is connected with the outlet of the bag type dust collector branch 235, and the screen drum branch port 256 is connected with the outlet of the screen drum branch 236. A feeding device on the feeding port 257 is a feeding valve 243, the discharging port 258 of the screw conveyor 237 is connected with the feeding port 246 on the circulating pipe I 231, and the air outlet of the fan 230 is connected with the inlet of the circulating pipe. The inlet gas treatment device 238 is a molecular sieve dryer, an air outlet of the molecular sieve dryer is connected with the air inlet of the fan through a supply air duct 239, the supply air duct 239 is further provided with a branch pipe for sending gas to a blowback air source supercharging device, the air inlet of the molecular sieve dryer is connected with the air outlet of the bag type dust collector branch through an inlet air pipe 240, and the air inlet of the molecular sieve dryer is further provided with a gas supply port 940 which is communicated with the outside of the apparatus.

When the circulating fluidized bed apparatus in Embodiment 1 is used for pollen pini processing, since part of pollen pini is subject to wall breaking, physical properties and conditions are subject to variation; due to the influence of consumption habits, the pollen pini with the physical properties and conditions subject to variation cannot be accepted by the market in a short term. In this embodiment, due to the fact that materials do not pass the fan, the problem that the circulating fluidized bed apparatus in Embodiment 1 breaks the pollen pini wall is solved to some extent; since the inlet gas treatment device is added, the problem of dust explosion hidden danger occurring when the circulating fluidized bed apparatus in Embodiment 1 is used for pollen pini processing is solved.

Figure 14:
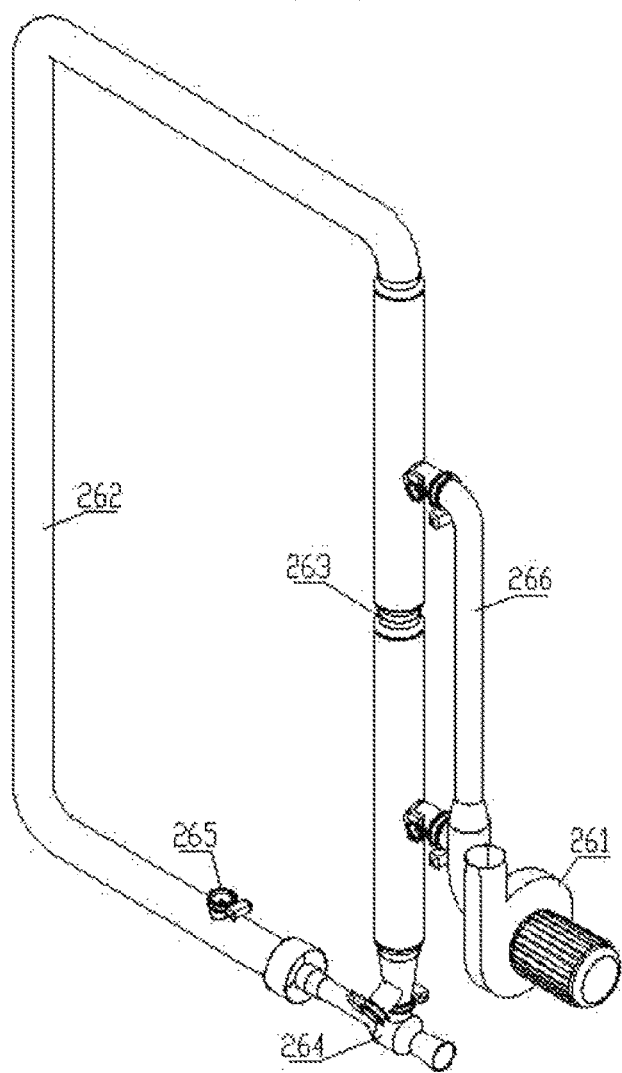
FIG. 14 is a structural drawing of a feeding fluidized bed dryer utilizing an ejector as a feeding pipe according to Embodiment 12.
Figure 15:
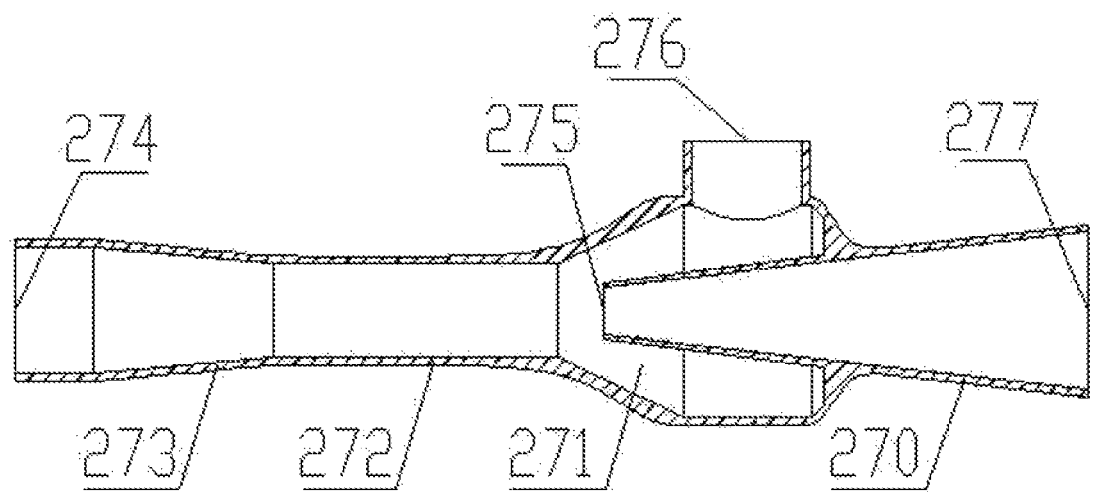
FIG. 15 is a structural drawing of an ejector embodiment.

Embodiment 12: A Negative Pressure Circulating Fluidized Bed Dryer Utilizing an Ejector as a Feeding Pipe Referring to FIGS. 14 and 15, in this embodiment, the negative pressure circulating fluidized bed dryer is composed of a circulating pipe 262, a bag type dust collector branch 263, an ejector 264, a pipe 266 and a fan 261. The bag type dust collector branch 263 has the same structure as the bag type dust collector branch in Embodiment 9. The head end of the circulating pipe 262 is an inlet, the tail end of the circulating pipe 262 is a bag type dust collector branch port which is connected with an inlet of the bag type dust collector branch 263, an outlet of the bag type dust collector branch 263 is connected with a suction inlet 276 of the ejector 264, a mixture outlet 274 of the ejector 264 is inserted into the inlet of the circulating pipe 262 to be communicated to form a circulating channel, an air inlet of the fan 261 is connected with the air outlet of the bag type dust collector branch 263 through a pipe 266, an ejector high-pressure fluid inlet 277 is communicated with a high pressure air source, a gap between a mixture outlet 274 of the suction inlet 276 and an inlet of the circulating pipe 262 is an air inlet of the apparatus in this embodiment, and a feeding port is arranged on the circulating pipe 262 and provided with a feeding valve 265.

Figure 16:
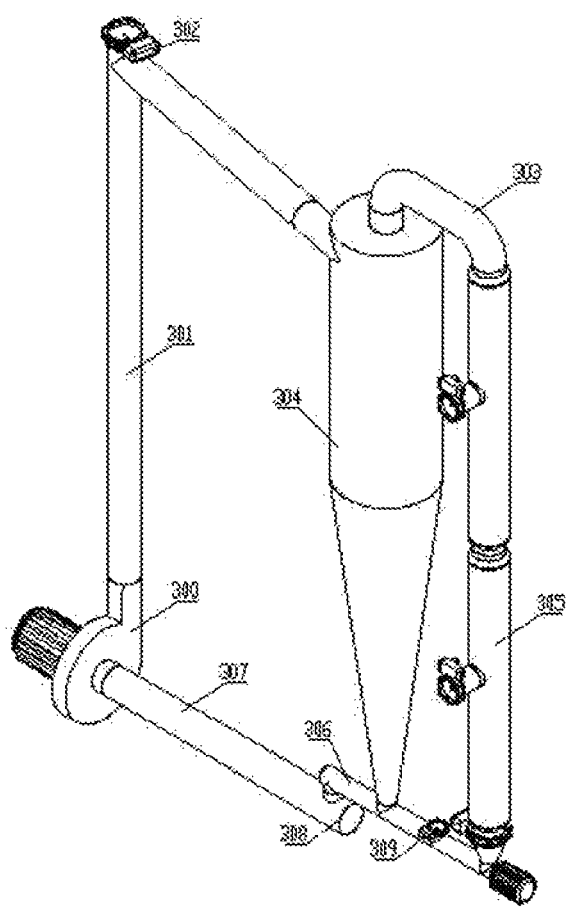
FIG. 16 is a structural drawing of a circulating fluidized bed air stream drying apparatus using a screw feeder for feeding according to Embodiment 13.

Embodiment 13: A Circulating Fluidized Bed Air Stream Drying Apparatus Using a Screw Feeder for Feeding Referring to FIG. 16, the circulating fluidized bed air stream drying apparatus using the screw feeder for feeding is composed of a fan 300, a circulating pipe, a cyclone dust collector branch, a bag type dust collector branch 305, a screw feeder 306 and a feeding pipe 307. The circulating pipe is composed of a circulating pipe I 301 and a circulating pipe II 303. The head end of the circulating pipe I 301 is an inlet of the circulating pipe, the circulating pipe I 301 is further provided with an outlet and a discharging port, and the discharging port is provided with a discharging valve 302. The head end of the circulating pipe II 303 is an inlet, the circulating pipe II 303 is further provided with a bag type dust collector branch port, the cyclone dust collector branch is composed of a cyclone dust collector 304, an air inlet of the cyclone dust collector 304 is an inlet of the cyclone dust collector branch, an ash discharging port of the cyclone dust collector 304 is an outlet of the cyclone dust collector branch, an air outlet of the cyclone dust collector 304 is an air outlet of the cyclone dust collector branch, and the cyclone dust collector branch is used for primary material-gas separation. The sectional area of the ash discharging port is one-twelfth that of the air inlet, the inlet of the cyclone dust collector branch is connected with the outlet of the circulating pipe I 301, the air outlet of the cyclone dust collector branch is connected with the inlet of the circulating pipe II 303, and the bag type dust collector branch 305 has the same structure as the bag type dust collector branch in Embodiment 1. The inlet of the bag type dust collector branch 305 is connected with the bag type dust collector branch port on the circulating pipe II 303, the tail end of a conveying pipe of the screw feeder 306 is provided with a discharging port, and the conveying pipe is further provided with a cyclone dust collector branch port, a bag type dust collector branch port and a feeding port. The feeding port is provided with a feeding valve 309, the cyclone dust collector branch port is connected with the cyclone dust collector branch outlet, and the bag type dust collector branch port is connected with the bag type dust collector branch outlet. The head end of the conveying pipe 307 is provided with an air inlet 308 in this embodiment, the tail end of the conveying pipe 307 is provided with an outlet, and the feeding pipe 307 is further provided with a functional branch port which is connected with the discharging port of the screw feeder 306. The outlet of the feeding pipe 307 is connected with the air inlet of the fan 300, and the air outlet of the fan 300 is connected with the inlet of the circulating pipe.

A screw feeder is adopted in this embodiment to feed to the feeding pipe at a constant speed the materials needing to be added and materials discharged out of the cyclone dust collector and the bag type dust collector branch, the problem that feeding unevenness occurring when the materials directly enter the feeding pipe leads to sharp fluctuation of a motor current is solved, the cyclone dust collector branch serves as a primary material-gas separating device to separate most of materials and air stream; compared with Embodiment 1, the burden on the bag type dust collector branch is relieved, and the geometric dimension of the bag type dust collector can be reduced.

Figure 17:
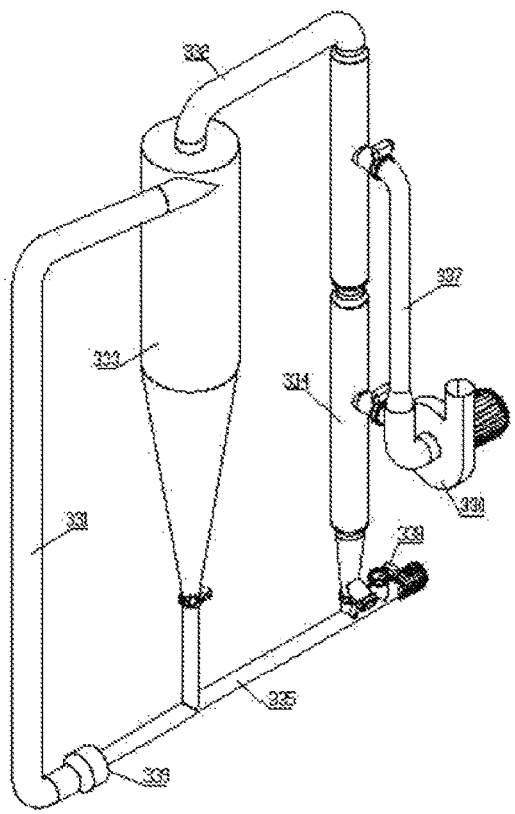
FIG. 17 is a structural drawing of a feeding fluidized bed air stream dryer using a screw conveyor as a feeding pipe according to Embodiment 14.

Embodiment 14: A Negative Pressure Circulating Fluidized Bed Air Stream Dryer Using a Screw Conveyor as a Feeding Pipe Referring to FIG. 17, the negative pressure circulating fluidized bed air stream dryer using the screw conveyor as the feeding pipe is composed of a fan 330, a pipe 337, a circulating pipe, a cyclone dust collector branch 333, a bag type dust collector branch 334 and a screw conveyor 335. The circulating pipe is composed of a circulating pipe I 331 and a circulating pipe II 332. The head end of the circulating pipe I 331 is provided with an inlet 339 of the circulating pipe, and the tail end of circulating pipe I 331 is provided with an outlet. The head end of the circulating pipe II 332 is provided with an inlet, and the circulating pipe II 332 is further provided with a bag type dust collector branch port. The cyclone dust collector branch is composed of a cyclone dust collector and an ash discharging valve mounted on an ash discharging port, an air inlet of the cyclone dust collector is an inlet of the cyclone dust collector branch, an outlet of the ash discharging valve is an outlet of the cyclone dust collector branch, an air outlet of the cyclone dust collector is an air outlet of the cyclone dust collector branch, and the cyclone dust collector is further provided with a discharging port which is further provided with a discharging valve. The cyclone dust collector branch is used for primary material-gas separation, the sectional area of the ash discharging port is one-twentieth that of the air inlet, the inlet of the cyclone dust collector branch is connected with the outlet of the circulating pipe I 331, the air outlet of the cyclone dust collector branch is connected with the inlet of the circulating pipe II 332, and the bag type dust collector branch 334 has the same structure as the bag type dust collector branch in Embodiment 9. The inlet of the bag type dust collector branch 334 is connected with the bag type dust collector branch port on the circulating pipe II 332, the tail end of a conveying pipe of the screw conveyor 335 is provided with a discharging port, and the conveying pipe is further provided with a cyclone dust collector branch port, a bag type dust collector branch port and a feeding port. The feeding port is provided with a feeding valve 338, the cyclone dust collector branch port is connected with the cyclone dust collector branch outlet, the bag type dust collector branch port is connected with the bag type dust collector branch outlet, the discharging port of the screw conveyor 335 is inserted into an inlet 339 of the circulating pipe, a gap between the discharging port of the screw conveyor 335 and the inlet 339 of the circulating pipe is an air inlet of the apparatus in this embodiment, and the air inlet of the fan 330 is connected with the air outlet of the bag type dust collector branch through the pipe 337.

Negative pressure operation is adopted in this embodiment, to-be-processed materials and materials discharged out of the functional branch are sent into the circulating pipe through the screw conveyor, and the materials do not pass through the fan.

Figure 18:
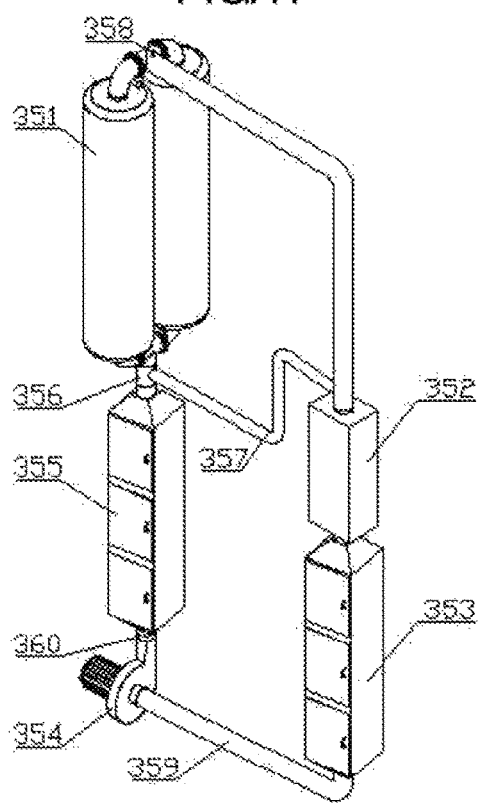
FIG. 18 is a structural drawing of a normal-temperature air stream drying apparatus which can achieve normal temperature drying, can maintain shapes of materials, can reduce loss of volatile ingredients in materials and restrain material oxidization according to Embodiment 15.
Figure 19:
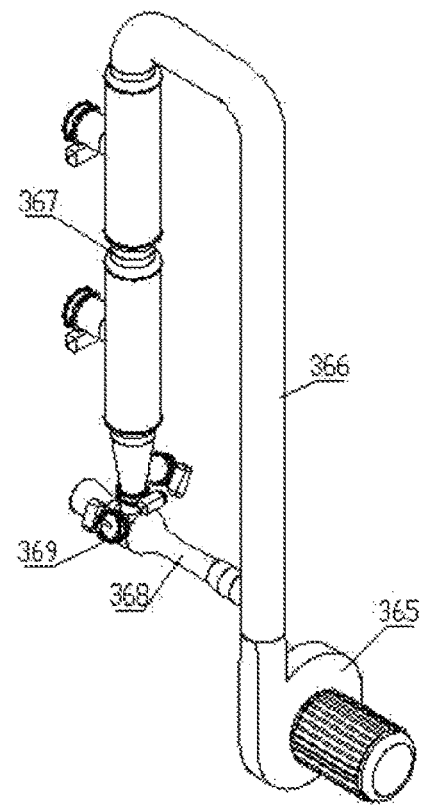
FIG. 19 is a structural drawing of a positive pressure circulating fluidized bed dryer using an ejector as a feeding pipe according to Embodiment 16.

Embodiment 15: A Normal-Temperature Air Stream Drying Apparatus which can Achieve Normal Temperature Drying, can Maintain Shapes of Materials, can Reduce Loss of Volatile Ingredients in Materials and Restrain Material Oxidization Referring to FIG. 18, in the embodiment, the apparatus is composed of a molecular sieve dryer 351, an air heater 352, a storage shelf 353, a feeding pipe 359, a fan 354, a circulating pipe 360, a storage shelf 355, an air pipe 356 and a pipe 357. An air outlet of the molecular sieve dryer 351 is further provided with a gas supply port 358 which is communicated with natural air outside the apparatus, the temperature of hot air output by the air heater 352 is below 50 degrees centigrade, and the storage shelf 353 and the storage shelf 355 are of the same structure, are airtight boxes with doors and are internally layered through grids. Materials are evenly fixed to the grids, gaps are reserved between the materials, and the sum of the areas of any cross section of the gaps is larger than the sectional area of the circulating pipe 360. The fan 354 is a power source and is used for conveying air stream having been dehydrated by the molecular sieve dryer 351 into the storage shelf 353 and the storage shelf 355 and makes the air stream pass the storage shelf 353 and the storage shelf 355 at a speed of 20 m/s. The air pipe 356 is used for sending exhaust discharged from the air outlet of the storage shelf 355 to the air inlet of the molecular sieve dryer 351 to serve as inlet air stream of the apparatus of this embodiment to be used. The sectional area of the pipe 357 is 10% that of the circulating pipe 360, and the pipe 357 is used for conveying gas with high volatile ingredient concentration at the inlet end of the molecular sieve dryer 351 to the outlet end of the molecular sieve dryer 351, so as to reduce the concentration difference of volatile ingredients between the inlet end of the storage shelf 353 and the outlet end of the storage shelf 355. The aforementioned components are communicated in such a sequence as the air outlet of the molecular sieve dryer 351, the air inlet of the air heater 352, the air outlet of the air heater 352, the air inlet of the storage shelf 353, the air outlet of the storage shelf 353, the functional branch port of the feeding pipe 359, the outlet of the feeding pipe 359, the air inlet of the fan 354, the air outlet of the fan 354, the inlet of the circulating pipe 360, the outlet of the circulating pipe 360, the air inlet of the storage shelf 355, the air inlet of the air pipe 356, the air outlet of the air pipe 356 and the air inlet of the molecular sieve dryer 351 to form a circulating channel, and the pipe 357 is connected between the air pipe 356 and the air outlet of the molecular sieve dryer 351.

In this embodiment, moisture and oxygen in a drying medium is separated through the molecular sieve dryer to increase the saturation deficit of water in the drying medium, the air heater is utilized to provide the drying medium at below 50 degrees centigrade, so as to achieve normal temperature drying, reduce oxidability of the drying medium and restrain material oxidization. Compared with the aforementioned embodiments, the materials are fixed to the grids and no longer pass the fan, so that the shapes of the materials are not damaged, and the drying medium does not leak; due to the increase of concentration of volatile ingredients, the saturation deficit of the volatile ingredients in the drying medium is reduced, the volatilization of the volatile ingredients is reduced, and the loss of the volatile ingredients in the dried materials can be reduced.

Embodiment 16: A Positive Pressure Circulating Fluidized Bed Dryer Using an Ejector as a Feeding Pipe Referring to FIG. 19, in this embodiment, the positive pressure circulating fluidized bed dryer is composed of a fan 365, a circulating pipe 366, a bag type dust collector branch 367 and an ejector 368. The bag type dust collector branch 367 is the same as the bag type dust collector branch in Embodiment 9. The head end of the circulating pipe 366 is provided with an inlet, the tail end of the circulating pipe 366 is provided with a bag type dust collector branch port, a feeding port is further disposed at the position of the circulating pipe 366 close to the inlet, the ejector 368 is provided with two suction inlets, one is a bag type dust collector branch port, and the other is a feeding port which is provided with a feeding valve 369. The air outlet of the fan 365 is connected with the inlet of the circulating pipe 366, the bag type dust collector branch port of the circulating pipe 366 is connected with the inlet of the bag type dust collector branch 367, the outlet of the bag type dust collector branch 367 is connected with the bag type dust collector branch port on the ejector 368, a mixture outlet of the ejector 368 is connected with the feeding port of the circulating pipe 366, a high-pressure fluid inlet of the ejector is communicated with a high pressure air source, and an air inlet of the fan 365 is an air inlet in this embodiment.

Embodiment 17: A Multi-Purpose Circulating Fluidized Bed Apparatus with a Molecular Sieve Dryer Branch Referring to FIG. 20, in this embodiment, the mufti-purpose circulating fluidized bed apparatus is formed by three improvements based on the closed loop circulating fluidized bed drying and distillation apparatus in Embodiment 9. 1. An exhaust treatment device is omitted, a molecular sieve dryer branch is added, a molecular sieve dryer branch port is added to the circulating pipe 370 and the molecular sieve dryer branch is formed by sequentially connecting an inlet valve 371 and a molecular sieve dryer 372; an air outlet of the molecular sieve dryer is provided with a gas supply port 373 which is connected with an inert gas source, the air outlet of the molecular sieve dryer is further provided with a port 378 connected with a blowback air source supercharging device; an inlet of the molecular sieve dryer branch is connected with the molecular sieve dryer branch port added to the circulating pipe, an inlet of the feeding pipe is the molecular sieve dryer branch port, a molecular sieve dryer outlet is connected with a feeding pipe inlet, and the inlet of the molecular sieve dryer 372 is further provided with an inlet air pipe to be connected with the air outlet of the bag type dust collector branch. 2. An air heater 374, a storage shelf 375 and a storage shelf 376 which are connected in sequence from the inlet of the feeding pipe are added to the feeding pipe. 3. A discharging tee and a mode of connecting the discharging tee with the feeding pipe are changed, an inlet of the discharging tee 381 is connected with an ash discharging port of a second bag type dust collector, and a second port of the discharging tee 381 is provided with a planet discharging valve 380; a regulating valve 379 is disposed on the third port of the discharging tee 381, a bend 382 is arranged in the discharging tee 381, one end of the bend 382 is connected to the third port in the discharging tee 381, the other end of the bend 382 is arranged in the second port in a suspended mode, and the planet discharging valve 380 is used for discharging materials.

In the maca processing process after harvest, two materials need to be treated, one is solid material fresh maca fruits or fresh maca fruit slices, and the other is a liquid material obtained through juicing or extraction. Products obtained through processing comprise maca powder, dried maca fruits and dried fruit slices. There are two maca processing requirements, one is that the processing needs to be performed at a normal temperature state, and the other is that the loss of volatile ingredients such as glucosinolate is reduced as far as possible. The apparatus in this embodiment can meet the maca processing requirements. 1. The liquid material obtained by juicing or extracting the fresh maca fruits is dried and ground, the inlet valve of the molecular sieve dryer branch is switched off, the material is added through an atomizer to undergo spray drying; after the drying is finished, the regulating valve of the bag type dust collector branch is switched off, and the material collected by the bag type dust collector branch is discharged out of the planet discharging valve. 2. The fresh maca fruits are dried and ground, the inlet valve of the molecular sieve dryer branch is switched off, and materials are added through the feeding valve to be processed. 3. The fresh maca fruits or fresh fruit slices are dried, the inlet valve of the molecular sieve dryer branch is switched on, a bypass valve of the cyclone dust collector branch is switched on to switch off an ash discharging valve of the cyclone dust collector branch so as to disconnect the cyclone dust collector branch, the regulating valve of the bag type dust collector branch is switched off to disconnect the bag type dust collector branch, and materials are fixed to the storage shelves to be dried. In the operation process, moisture produced by drying is separated and discharged through the molecular sieve dryer and is supplied to a drying medium of the apparatus with a very low water content so as to quicken the drying speed, and the drying medium does not leak out; the volatilization of the glucosinolate makes the concentration of glucosinolate in the drying medium increased, and an effect of restraining further volatilization can be achieved, and the temperature of hot air output by the air heater is controlled to make the material temperature not exceed 50 degrees centigrade so as to achieve normal temperature drying. The apparatus in this embodiment can also be used for processing other medicine and food materials which have the same processing requirements as maca.

In this embodiment, under the conditions of no considering of reducing the loss of volatile ingredients, the inlet valve in the molecular sieve dryer branch may be disconnected with the molecular sieve dryer, natural air outside the apparatus is adopted as inlet air, and the moisture separation pressure over the molecular sieve dryer can be reduced on the conditions that the air humidity outside the apparatus is small.

What is claimed is:

1. A circulating fluidized bed apparatus, comprising a fan, a circulating pipe, a functional branch and a feeding pipe, wherein the fan is a power device and is used for dispersing materials into a fluidized state and making the materials circulate and flow at a high speed in a circulating channel;

the head end of the circulating pipe is an inlet of the circulating pipe, and the circulating pipe is provided with a functional branch port;

the functional branch is used for achieving specific process objectives; the head end of the functional branch is an inlet, and the tail end of the functional branch is an outlet; the functional branch is one or more selected from a group comprising a bag type dust collector branch, a screen drum branch, and a molecular sieve branch; the bag type dust collector branch at least comprises a bag type dust collector and is formed by partially or all connecting an inlet valve, a conveying tee, the bag type dust collector, a discharging tee and a regulating valve in sequence, an air inlet of the bag type dust collector is an inlet of the bag type dust collector, an ash discharging port of the bag type dust collector is an outlet of the bag type dust collector, an air outlet of the bag type dust collector is an inlet of the bag type dust collector branch; the screen drum branch at least comprises a screen drum and is formed by partially or all connecting an inlet valve, the screen drum, a slag-discharging tee and a regulating port of the screen drum is an outlet of the screen drum is an intel of the screen drum, an ash discharging port of the screen drum is an outlet of the screen drum; an air outlet of the screen drum is both the air outlet of the screen drum and a screen underflow discharging port and is also an air outlet of the screen drum branch; the molecular sieve dryer branch at least comprises a molecular sieve dryer and is formed by partially or all connecting an intel valve, the molecular sieve dryer and a regulating valve in sequence; an inlet of a head end component of the functional branch is an inlet of the functional branch, and an outlet of a tail end component of the functional branch is an outlet of the functional branch;

the feeding pipe is used for feeding to the circulating pipe the materials discharged out of the functional branch port; the head end of the feeding pipe is an inlet of the feeding pipe and is also an air inlet of the circulating fluidized bed apparatus, and the tail end of the feeding pipe is an outlet of the feeding pipe; the feeding pipe is provided with a functional branch port and a feeding port, and the feeding port is provided with a feeding device;

the aforementioned components are communicated in such a sequence as the air outlet of the fan, the inlet of the circulating pipe, the functional branch port of the circulating pipe, the inlet of the functional branch, the outlet of the functional branch, the functional branch port of the feeding pipe, the outlet of the feeding pipe and the air inlet of the fan to form the circulating channel.

2. The circulating fluidized bed apparatus according to claim 1, wherein the functional branch includes a cyclone dust collector branch, the cyclone dust collector branch at least comprises a cyclone dust collector and is formed by partially or all connecting an inlet valve, the cyclone dust collector and an ash discharging valve installed on an ash discharging port of the cyclone dust collector in sequence; an air inlet of the cyclone dust collector is an inlet of the cyclone dust collector, an ash discharging port of the cyclone dust collector is an outlet of the cyclone dust collector, an air outlet of the cyclone dust collector is both the air outlet of the cyclone dust collector and an air outlet of the cyclone dust collector branch; and/or a third port of the conveying tee of the cyclone dust collector is provided with a conveying valve, and a third port of the discharging tee of the cyclone dust collector is provided with a discharging valve; and/or a third port of the slag-discharging tee of the screen drum branch is provided with a slag-discharging valve.

3. The circulating fluidized bed apparatus according to claim 1, wherein the feeding device is a feeding valve or/and an atomizer or a feeder or an extruding machine; the atomizer is used for feeding liquid materials; the feeder is preferably a screw feeder and is used for feeding to-be-processed materials and/or materials separated from the functional branch into the feeding pipe at a constant speed; when the screw feeder is used for feeding the to-be-processed materials and/or the materials separated from the functional branch into the feeding pipe at a constant speed, a conveying pipe of the screw feeder is provided with a functional branch port, a feeding port and a discharging port; the functional branch port is connected with the functional branch outlet, and the discharging port is connected with the functional branch port on the feeding pipe; and the extruding machine is used for causing materials which are difficult to disperse and cannot be pumped to be extruded into a line shape and feeding the materials into the feeding pipe.

4. The circulating fluidized bed apparatus according to claim 1, wherein the feeding pipe is a conveyor which is a screw conveyor, and a conveying pipe of the screw conveyor is provided with a functional branch port and a discharging port; all the components are communicated in such a sequence as the functional branch port of the circulating pipe, the functional branch inlet, the functional branch outlet, the functional branch port of the screw conveyor and the discharging port of the screw conveyor inserted into the inlet of the circulating pipe so as to form the circulating channel; the air inlet of the fan is connected with the air outlet of the functional branch through a pipe, the gap between the discharging port of the screw conveyor and the inlet of the circulating pipe is an air inlet of the circulating fluidized bed apparatus, and the feeding port is arranged on the conveying pipe of the screw conveyor or the circulating pipe; or, a feeding port is at the position of the circulating pipe close to the inlet, the feeding pipe is a screw conveyor, a conveying pipe of the screw conveyor is provided with a functional branch port and a discharging port; all the components are communicated in such a sequence as the functional branch port of the circulating pipe, the inlet of the functional branch, the outlet of the functional branch, the functional branch port of the screw conveyor, the discharging port of the screw conveyor and the feeding port of the circulating pipe to form the circulating channel; the air outlet of the fan is connected with the inlet of the circulating pipe, the air inlet of the fan is an air inlet of the circulating fluidized bed apparatus, and a feeding port is arranged on the conveying pipe of the screw conveyor.

5. The circulating fluidized bed apparatus according to claim 1, wherein the feeding pipe is an ejector which is provided with a suction inlet, a mixture outlet and a high-pressure fluid inlet; the suction inlet is a functional branch port of the feeding pipe; all the components are communicated in such a sequence as the functional branch port of the circulating pipe, the inlet of the functional branch, the outlet of the functional branch, the suction inlet and the mixture outlet inserted into the inlet of the circulating pipe so as to form the circulating channel, the air inlet of the fan is connected with the air outlet of the functional branch through a pipe, the high-pressure fluid inlet is communicated with a high pressure air source, the gap between the mixture outlet and the inlet of the circulating pipe is an air inlet of the circulating fluidized bed apparatus, and the feeding port is arranged on the suction inlet or the circulating pipe; or, a feeding port is arranged at the position of the circulating pipe close to the inlet, and the feeding pipe is an ejector which is provided with a suction inlet, a mixture outlet and a high-pressure fluid inlet; the suction inlet is a functional branch port of the feeding pipe, and all the components are communicated in such a sequence as the functional branch port of the circulating pipe, the inlet of the functional branch, the outlet of the functional branch, the suction inlet, the mixture outlet and the feeding port of the circulating pipe to form a circulating channel; the air outlet of the fan is connected with the inlet of the circulating pipe, the high-pressure fluid inlet is communicated with the high pressure air source, the air inlet of the fan is an air inlet of the circulating fluidized bed apparatus, and the feeding port is arranged on the suction inlet.

6. The circulating fluidized bed apparatus according to claim 1, wherein the circulating pipe is further provided with a discharging port, and the discharging port is provided with a discharging valve; and/or, in the circulating fluidized bed apparatus with a bag type dust collector branch, the bag type dust collector branch is disconnected with the feeding pipe and a planet discharging valve is added at the tail end of the bag type dust collector branch, and materials collected by the bag type dust collector branch are discharged out of the planet discharging valve; or, an inlet of a discharging tee of the bag type dust collector branch is connected with an ash discharging port of the bag type dust collector, a second port of the discharging tee is provided with a planet discharging valve, a regulating valve is arranged on a third port of the discharging tee; a bend is arranged in the discharging tee, one end of the bend is connected with the third port inside the discharging tee, and the other end of the bend is arranged in the second port in a suspended mode, and materials collected by the bag type dust collector branch are discharged through the planet discharging valve; and/or, in the circulating fluidized bed apparatus with the screen drum branch, an inlet of a slag-discharging tee of the screen drum branch is connected with the ash-discharging port of the screen drum, the second port of the slag-discharging tee is provided with a planet discharging valve, a regulating valve is arranged on the third port of the slag-discharging tee, a bend is arranged in the stag-discharging tee, one end of the bend is connected with the third port inside the slag-discharging tee, the other end of the bend is arranged in the second port in a suspended mode, and materials collected by the screen drum branch are discharged through the planet discharging valve.

7. The circulating fluidized bed apparatus according to claim 2, wherein the cyclone dust collector is provided with a discharging port, and the discharging port is provided with a discharging valve.

8. The circulating fluidized bed apparatus according to claim 1, wherein a mill and a feeding pipe rear section are arranged between the outlet of the feeding pipe and the fan; the feeding pipe rear section is vertically arranged and is a variable diameter pipe, and the pipe diameter of the inlet end is larger than that of the outlet end; the outlet of the feeding pipe is connected with a feeding port of the mill, a discharging port of the mill is connected with an inlet of the feeding pipe rear section, an outlet of the feeding pipe rear section is connected with the air inlet of the fan, and the feeding port on the feeding pipe is next to the outlet of the feeding pipe.

9. The circulating fluidized bed apparatus according to claim 1, wherein the circulating fluidized bed apparatus further comprises a regulating device; the regulating device comprises an inlet air stream temperature regulating device and/or a fan rotating speed regulating device; the inlet air stream temperature regulating device controls the temperature of inlet air stream through output signals of a temperature sensor installed on the circulating pipe, so that the temperature inside the apparatus does not exceed a set temperature; and the fan rotating speed regulating device is used for regulating the rotating speed of the fan so as to control heat produced by converting kinetic energy of the fan, so that the temperature inside the apparatus does not exceed a set temperature.

10. The circulating fluidized bed apparatus according to claim 1, wherein an ultraviolet sterilization lamp tube for achieving ultraviolet sterilization of powdered materials is installed in the circulating channel of the circulating fluidized bed apparatus.

11. The circulating fluidized bed apparatus according to claim 1, wherein the air outlet of the bag type dust collector branch is further provided with an exhaust treatment device, an inlet of the exhaust treatment device is connected with the air outlet of the bag type dust collector branch through a pipe, and the exhaust treatment device is a condenser or a device for collecting specific ingredients.

12. The circulating fluidized bed apparatus according to claim 2, wherein in the apparatus with the cyclone dust collector branch, the circulating pipe is divided into two sections, one section is a circulating pipe I, and the other section is a circulating pipe II; the inlet of the cyclone dust collector branch is connected with an outlet of the circulating pipe I, the air outlet of the cyclone dust collector is connected with an inlet of the circulating pipe II, an inlet of the circulating pipe I is the inlet of the circulating pipe, and other functional branch ports are arranged on the circulating pipe II.

13. The circulating fluidized bed apparatus according to claim 1, wherein in the circulating fluidized bed apparatus with a molecular sieve dryer branch, the circulating pipe and/or the feeding pipe is further provided with a storage shelf which is used for placing materials needing to be dried, the storage shelf is an airtight box with a door and is internally layered through grids, and the materials are evenly fixed to the grids; gaps are reserved between the materials, and the sum of the areas of any cross section of the gaps is kept larger than the sectional area of the circulating pipe.

14. The circulating fluidized bed apparatus according to claim 2, wherein when the cyclone dust collector branch is used for impurity separation and material classification, the ratio of the diameter of a barrel of the cyclone dust collector to the height of a cone is larger than 1, and a separating drum for separating lower vortex air stream and upper vortex air stream is arranged in the barrel; the upper end of the separating drum is connected with an upper end cover of the cyclone dust collector, and the lower end of the separating drum extends into the cone; and when the cyclone dust collector branch serves as a primary material-gas separation device, the ratio of the sectional area of the air inlet of the cyclone dust collector to the sectional area of the ash discharging port is larger than 2.

* * * * *